US010905396B2

(12) United States Patent
Cox et al.

(10) Patent No.: US 10,905,396 B2
(45) Date of Patent: Feb. 2, 2021

(54) ULTRASOUND IMAGING SYSTEM HAVING AUTOMATIC IMAGE PRESENTATION

(71) Applicant: C.R. Bard, Inc., Tempe, AZ (US)

(72) Inventors: Jeremy B. Cox, Salt Lake City, UT (US); Michael A. Randall, Gilbert, AZ (US); Peng Zheng, Chandler, AZ (US); Dean M. Addison, Victoria (CA); Bryan A. Matthews, Saanichton (CA)

(73) Assignee: C. R. Bard, Inc., Franklin Lakes, NJ (US)

( * ) Notice: Subject to any disclaimer, the term of this patent is extended or adjusted under 35 U.S.C. 154(b) by 349 days.

(21) Appl. No.: 15/525,307

(22) PCT Filed: Feb. 27, 2015

(86) PCT No.: PCT/US2015/018068
§ 371 (c)(1),
(2) Date: May 9, 2017

(87) PCT Pub. No.: WO2016/081023
PCT Pub. Date: May 26, 2016

(65) Prior Publication Data
US 2018/0296185 A1     Oct. 18, 2018

Related U.S. Application Data

(60) Provisional application No. 62/081,275, filed on Nov. 18, 2014.

(51) Int. Cl.
*A61B 8/00*     (2006.01)
*A61B 8/08*     (2006.01)

(52) U.S. Cl.
CPC .......... *A61B 8/4254* (2013.01); *A61B 8/0841* (2013.01); *A61B 8/4263* (2013.01);
(Continued)

(58) Field of Classification Search
CPC ... A61B 8/0841; A61B 8/4254; A61B 8/4263; A61B 8/4405; A61B 8/4461; A61B 8/461; A61B 8/466; A61B 8/483; A61B 8/5246
See application file for complete search history.

(56) References Cited

U.S. PATENT DOCUMENTS

| 3,927,661 A | 12/1975 | Takemura |
| 4,362,059 A | 12/1982 | Zwyssig |

(Continued)

FOREIGN PATENT DOCUMENTS

| WO | 2014099825 A3 | 6/2014 |
| WO | 2016081023 A1 | 5/2016 |
| WO | 2016081321 A2 | 5/2016 |

OTHER PUBLICATIONS

Anonymous: "Aurora", Retrieved from the Internet: http://www.ndigital.com/medical/products/aurora, retrieved on Jun. 30, 2015.
(Continued)

*Primary Examiner* — Michael T Rozanski

(57) ABSTRACT

An ultrasound imaging system includes an interventional medical device having a first tracking element that generates tip location data based on an EM locator field. An ultrasound probe has an ultrasound transducer mechanism and a second tracking element. The ultrasound transducer mechanism has an active ultrasound transducer array that generates two-dimensional ultrasound slice data at any of a plurality of discrete imaging locations within a three-dimensional imaging volume. The second tracking element generates probe location data based on the EM locator field. A processor circuit is configured to execute program instructions to generate an ultrasound image for display, and is configured to generate a positioning signal based on the tip location data and the probe location data to dynamically position the active ultrasound transducer array so that the two-dimen-
(Continued)

sional ultrasound slice data includes the distal tip of the interventional medical device.

20 Claims, 17 Drawing Sheets

(52) U.S. Cl.
CPC ............ *A61B 8/483* (2013.01); *A61B 8/5246* (2013.01); *A61B 8/4405* (2013.01); *A61B 8/4461* (2013.01); *A61B 8/461* (2013.01); *A61B 8/466* (2013.01)

(56) References Cited

U.S. PATENT DOCUMENTS

| | | | |
|---|---|---|---|
| 4,431,007 A | 2/1984 | Amazeen et al. |
| 4,483,344 A | 11/1984 | Atkov et al. |
| 4,669,482 A | 6/1987 | Ophir |
| 4,796,632 A | 1/1989 | Boyd et al. |
| 4,821,731 A | 4/1989 | Martinelli et al. |
| 4,831,601 A | 5/1989 | Breimesser et al. |
| 4,920,966 A | 5/1990 | Hon et al. |
| 4,974,593 A | 12/1990 | Ng |
| 5,094,243 A | 3/1992 | Puy et al. |
| 5,152,294 A | 10/1992 | Mochizuki et al. |
| 5,191,889 A | 3/1993 | Mornhinweg et al. |
| 5,335,663 A * | 8/1994 | Oakley .................. A61B 8/12 600/459 |
| 5,381,794 A | 1/1995 | Tei et al. |
| 5,460,179 A | 10/1995 | Okunuki et al. |
| 5,503,152 A | 4/1996 | Oakley et al. |
| 5,598,845 A | 2/1997 | Chandraratna et al. |
| 5,615,680 A | 4/1997 | Sano |
| 5,626,554 A | 5/1997 | Ryaby et al. |
| 5,669,385 A | 9/1997 | Pesque et al. |
| 5,701,897 A | 12/1997 | Sano |
| 5,715,825 A | 2/1998 | Crowley |
| 5,727,553 A | 3/1998 | Saad |
| 5,769,843 A | 6/1998 | Abela et al. |
| 5,860,929 A | 1/1999 | Rubin et al. |
| 6,048,323 A | 4/2000 | Hon |
| 6,080,108 A | 6/2000 | Dunham |
| 6,132,376 A | 10/2000 | Hossack et al. |
| 6,132,378 A | 10/2000 | Marino |
| 6,241,667 B1 | 6/2001 | Vetter et al. |
| 6,241,675 B1 | 6/2001 | Smith et al. |
| 6,248,074 B1 | 6/2001 | Dhno et al. |
| 6,261,231 B1 | 7/2001 | Damphousse et al. |
| 6,263,093 B1 | 7/2001 | Mochizuki |
| 6,413,218 B1 | 7/2002 | Allison et al. |
| 6,423,006 B1 | 7/2002 | Banjanin |
| 6,464,642 B1 | 10/2002 | Kawagishi |
| 6,517,481 B2 | 2/2003 | Hoek et al. |
| 6,524,303 B1 | 2/2003 | Garibaldi |
| 6,527,718 B1 | 3/2003 | Connor et al. |
| 6,565,513 B1 | 5/2003 | Phillips |
| 6,587,709 B2 | 7/2003 | Solf et al. |
| 6,600,948 B2 | 7/2003 | Ben-haim et al. |
| 6,684,094 B1 | 1/2004 | Lehr et al. |
| 6,685,644 B2 | 2/2004 | Seo et al. |
| 6,690,963 B2 | 2/2004 | Ben-haim et al. |
| 6,716,166 B2 | 4/2004 | Govari |
| 6,735,465 B2 | 5/2004 | Panescu |
| 6,755,789 B2 | 6/2004 | Stringer et al. |
| 6,757,557 B1 | 6/2004 | Bladen et al. |
| 6,772,001 B2 | 8/2004 | Maschke |
| 6,773,402 B2 | 8/2004 | Govari et al. |
| 6,884,216 B2 | 4/2005 | Abe et al. |
| 6,895,267 B2 | 5/2005 | Panescu et al. |
| 6,951,543 B2 | 10/2005 | Roundhill |
| 6,970,733 B2 | 11/2005 | Willis et al. |
| 6,988,991 B2 | 1/2006 | Kim et al. |
| 7,010,338 B2 | 3/2006 | Ritter et al. |
| 7,051,738 B2 | 5/2006 | Dron et al. |
| 7,081,093 B2 | 7/2006 | Flesch |
| 7,090,639 B2 | 8/2006 | Govari |
| 7,194,294 B2 | 3/2007 | Panescu et al. |
| 7,197,354 B2 | 3/2007 | Sobe |
| 7,214,191 B2 | 5/2007 | Stringer et al. |
| 7,311,679 B2 | 12/2007 | Desilets et al. |
| 7,364,546 B2 | 4/2008 | Panescu et al. |
| 7,433,504 B2 | 10/2008 | Deischinger et al. |
| 7,477,763 B2 | 1/2009 | Willis et al. |
| 7,493,154 B2 | 2/2009 | Bonner et al. |
| 7,517,318 B2 | 4/2009 | Altmann et al. |
| 7,520,857 B2 | 4/2009 | Chalana et al. |
| 7,536,218 B2 | 5/2009 | Govari et al. |
| 7,555,330 B2 | 6/2009 | Gilboa et al. |
| 7,604,601 B2 | 10/2009 | Altmann et al. |
| 7,637,885 B2 | 12/2009 | Maschke |
| 7,677,078 B2 | 3/2010 | Sauer et al. |
| 7,686,767 B2 | 3/2010 | Maschke |
| 7,713,210 B2 | 5/2010 | Byrd et al. |
| 7,735,349 B2 | 6/2010 | Hochmitz |
| 7,740,584 B2 | 6/2010 | Donaldson et al. |
| 7,749,168 B2 | 7/2010 | Maschke et al. |
| 7,766,833 B2 | 8/2010 | Lee et al. |
| 7,766,836 B2 | 8/2010 | Waki |
| 7,769,427 B2 | 8/2010 | Shachar |
| 7,774,043 B2 | 8/2010 | Mills |
| 7,778,688 B2 | 8/2010 | Strommer |
| 7,803,116 B2 | 9/2010 | Sikdar et al. |
| 7,806,828 B2 | 10/2010 | Stringer |
| 7,806,829 B2 | 10/2010 | Hauck |
| 7,819,810 B2 | 10/2010 | Stringer et al. |
| 7,822,464 B2 | 10/2010 | Maschke et al. |
| 7,831,076 B2 | 11/2010 | Altmann et al. |
| 7,837,625 B2 | 11/2010 | Abe |
| 7,848,789 B2 | 12/2010 | Govari et al. |
| 7,854,237 B2 | 12/2010 | Hand |
| 7,871,379 B2 | 1/2011 | Ohtsuka |
| 7,873,401 B2 | 1/2011 | Shachar |
| 7,881,769 B2 | 2/2011 | Sobe |
| 7,927,279 B2 | 4/2011 | Kubota et al. |
| 7,938,847 B2 | 5/2011 | Fanton et al. |
| 7,961,924 B2 | 6/2011 | Viswanathan |
| 7,967,808 B2 | 6/2011 | Fitzgerald et al. |
| 7,969,142 B2 | 6/2011 | Krueger et al. |
| 7,981,038 B2 | 7/2011 | Kanade et al. |
| 7,996,057 B2 | 8/2011 | Govari et al. |
| RE42,856 E | 10/2011 | Karmarkar et al. |
| 8,041,411 B2 | 10/2011 | Camus |
| 8,041,413 B2 | 10/2011 | Barbagli et al. |
| 8,082,021 B2 | 12/2011 | Hyde et al. |
| 8,086,298 B2 | 12/2011 | Whitmore, III et al. |
| 8,126,534 B2 | 2/2012 | Maschke |
| 8,167,810 B2 | 5/2012 | Maschke |
| 8,172,757 B2 | 5/2012 | Jaffe et al. |
| 8,175,682 B2 | 5/2012 | Hamm et al. |
| 8,196,471 B2 | 6/2012 | Han et al. |
| 8,206,404 B2 | 6/2012 | De La Rama et al. |
| 8,211,025 B2 | 7/2012 | Donaldson et al. |
| 8,212,554 B2 | 7/2012 | Brazdeikis et al. |
| 8,214,015 B2 | 7/2012 | Macaulay et al. |
| 8,216,149 B2 | 7/2012 | Oonuki et al. |
| 8,228,347 B2 | 7/2012 | Beasley et al. |
| 8,257,261 B2 | 9/2012 | Kawae |
| RE43,750 E | 10/2012 | Martinelli |
| 8,292,817 B2 | 10/2012 | Mori |
| 8,298,149 B2 | 10/2012 | Hastings et al. |
| 8,303,507 B2 | 11/2012 | Baba et al. |
| 8,320,711 B2 | 11/2012 | Altmann et al. |
| 8,332,013 B2 | 12/2012 | Strommer |
| 8,335,555 B2 | 12/2012 | Lehman |
| 8,343,052 B2 | 1/2013 | Kawagishi et al. |
| 8,359,086 B2 | 1/2013 | Maschke |
| 8,366,738 B2 | 2/2013 | Dehnad |
| 8,388,541 B2 | 3/2013 | Messerly et al. |
| 8,388,546 B2 | 3/2013 | Rothenberg |
| 8,412,311 B2 | 4/2013 | Kenneth |
| 8,428,690 B2 | 4/2013 | Li et al. |
| 8,428,691 B2 | 4/2013 | Byrd et al. |
| 8,439,840 B1 | 5/2013 | Duffy |

(56) References Cited

U.S. PATENT DOCUMENTS

| | | |
|---|---|---|
| 8,452,376 B2 | 5/2013 | Elgort et al. |
| 8,473,029 B2 | 6/2013 | Gerhart et al. |
| 8,475,524 B2 | 7/2013 | Schwartz |
| 8,478,382 B2 | 7/2013 | Burnside et al. |
| 8,480,588 B2 | 7/2013 | Kanade et al. |
| 8,485,976 B2 | 7/2013 | Iimura et al. |
| 8,496,586 B2 | 7/2013 | Zhang et al. |
| 8,512,256 B2 | 8/2013 | Rothenberg |
| 8,527,032 B2 | 9/2013 | Li |
| 8,535,229 B2 | 9/2013 | Umemura et al. |
| 8,577,105 B2 | 11/2013 | Abe et al. |
| 8,591,417 B2 | 11/2013 | Suzuki et al. |
| 8,634,619 B2 | 1/2014 | Yoshiara et al. |
| 8,670,816 B2 | 3/2014 | Green et al. |
| 8,693,011 B2 | 4/2014 | Mori |
| 8,781,555 B2 | 7/2014 | Burnside et al. |
| 8,801,693 B2 | 8/2014 | He et al. |
| 8,857,263 B2 | 10/2014 | Both et al. |
| 8,867,808 B2 | 10/2014 | Satoh et al. |
| 8,900,149 B2 | 10/2014 | Satoh et al. |
| 8,885,897 B2 | 11/2014 | Xu et al. |
| 8,945,147 B2 | 2/2015 | Ritchey et al. |
| 8,971,600 B2 | 3/2015 | Yoshikawa et al. |
| 9,005,127 B2 | 4/2015 | Azuma |
| 9,024,624 B2 | 5/2015 | Brunner |
| 9,055,883 B2 | 6/2015 | Tgavalekos et al. |
| 9,082,178 B2 | 7/2015 | Hyun et al. |
| 9,107,607 B2 | 8/2015 | Hansegard et al. |
| 9,119,557 B2 | 9/2015 | Masui et al. |
| 9,149,568 B2 | 10/2015 | Gerg et al. |
| 9,173,638 B2 | 11/2015 | Govari et al. |
| 9,216,299 B2 | 12/2015 | Wolfe |
| 9,220,480 B2 | 12/2015 | Lee et al. |
| 9,241,683 B2 | 1/2016 | Slayton et al. |
| 9,256,947 B2 | 2/2016 | Gauthier et al. |
| 9,282,324 B2 | 3/2016 | Hamada |
| 9,289,187 B2 | 3/2016 | Owen et al. |
| 9,295,449 B2 | 3/2016 | Zhang et al. |
| 9,307,954 B2 | 4/2016 | Nishigaki |
| 9,308,041 B2 | 4/2016 | Altmann et al. |
| 9,314,222 B2 | 4/2016 | Creighton, IV et al. |
| 9,332,965 B2 | 5/2016 | Lee et al. |
| 9,375,163 B2 | 6/2016 | Ludwin et al. |
| 9,380,999 B2 | 7/2016 | Yoshida et al. |
| 9,390,495 B2 | 7/2016 | Lee et al. |
| 9,439,624 B2 | 9/2016 | Caluser |
| 9,445,780 B2 | 9/2016 | Hossack et al. |
| 9,451,933 B2 | 9/2016 | Duffy |
| 9,456,766 B2 | 10/2016 | Cox et al. |
| 9,474,465 B2 | 10/2016 | Ashe |
| 9,492,104 B2 | 11/2016 | Clark et al. |
| 9,521,961 B2 | 12/2016 | Silverstein et al. |
| 9,554,716 B2 | 1/2017 | Burnside et al. |
| 9,572,549 B2 | 2/2017 | Belevich et al. |
| 9,612,142 B2 | 4/2017 | Kristofferson et al. |
| 9,649,048 B2 | 5/2017 | Cox et al. |
| 2002/0019644 A1 | 2/2002 | Hastings et al. |
| 2004/0015079 A1 | 1/2004 | Berger et al. |
| 2004/0097803 A1 | 5/2004 | Panescu |
| 2004/0249287 A1 | 12/2004 | Kawashima et al. |
| 2005/0021063 A1 | 1/2005 | Hall et al. |
| 2005/0027195 A1 | 2/2005 | Govari |
| 2005/0085718 A1 | 4/2005 | Shahidi |
| 2005/0131289 A1 | 6/2005 | Aharoni et al. |
| 2006/0004291 A1 | 1/2006 | Heimdal et al. |
| 2006/0173304 A1 | 8/2006 | Wang |
| 2006/0174065 A1 | 8/2006 | Kuzara et al. |
| 2006/0184029 A1 | 8/2006 | Haim et al. |
| 2006/0241461 A1 | 10/2006 | White et al. |
| 2006/0247522 A1 | 11/2006 | Mcgee |
| 2006/0253031 A1 | 11/2006 | Altmann et al. |
| 2007/0167769 A1 | 7/2007 | Ikuma et al. |
| 2007/0213616 A1 | 9/2007 | Anderson et al. |
| 2007/0238979 A1 | 10/2007 | Huynh et al. |
| 2008/0021297 A1 | 1/2008 | Boosten |
| 2008/0039725 A1 | 2/2008 | Man et al. |
| 2008/0051652 A1 | 2/2008 | Ichioka et al. |
| 2008/0161840 A1 | 7/2008 | Osiroff et al. |
| 2008/0294037 A1 | 11/2008 | Richter |
| 2009/0018448 A1 | 1/2009 | Seo et al. |
| 2009/0093712 A1 | 4/2009 | Busch et al. |
| 2009/0105579 A1 | 4/2009 | Garibaldi |
| 2009/0118620 A1 | 5/2009 | Tgavalekos et al. |
| 2009/0131797 A1 | 5/2009 | Jeong et al. |
| 2009/0137900 A1 | 5/2009 | Bonner et al. |
| 2009/0143676 A1 | 6/2009 | Matsumura |
| 2009/0163810 A1 | 6/2009 | Kanade et al. |
| 2009/0192385 A1 | 7/2009 | Meissner et al. |
| 2009/0306497 A1 | 12/2009 | Manzke et al. |
| 2010/0016726 A1 | 1/2010 | Meier |
| 2010/0049052 A1 | 2/2010 | Shari et al. |
| 2010/0063398 A1* | 3/2010 | Halmann ............ A61B 8/0833 600/459 |
| 2010/0113919 A1 | 5/2010 | Maschke |
| 2010/0160781 A1 | 6/2010 | Carter et al. |
| 2010/0191101 A1 | 7/2010 | Lichtenstein |
| 2010/0222680 A1 | 9/2010 | Hamada |
| 2010/0249602 A1 | 9/2010 | Buckley et al. |
| 2010/0298713 A1 | 11/2010 | Robinson |
| 2011/0092862 A1 | 4/2011 | Chivers |
| 2011/0125022 A1 | 5/2011 | Lazebnik |
| 2011/0142319 A1 | 6/2011 | Lee et al. |
| 2011/0194748 A1 | 8/2011 | Tonomura et al. |
| 2011/0196238 A1 | 8/2011 | Jacobson et al. |
| 2011/0196397 A1 | 8/2011 | Frantz et al. |
| 2011/0224550 A1 | 9/2011 | Shinohara |
| 2011/0230763 A1 | 9/2011 | Emery et al. |
| 2011/0230796 A1 | 9/2011 | Emery et al. |
| 2011/0255762 A1 | 10/2011 | Deischinger et al. |
| 2011/0301460 A1 | 12/2011 | Anite |
| 2012/0046553 A9 | 2/2012 | Buckley et al. |
| 2012/0065499 A1 | 3/2012 | Chono |
| 2012/0070051 A1 | 3/2012 | Vincent et al. |
| 2012/0071752 A1 | 3/2012 | Sewell et al. |
| 2012/0143029 A1 | 6/2012 | Silverstein et al. |
| 2012/0165671 A1 | 6/2012 | Hill et al. |
| 2012/0197113 A1 | 8/2012 | Courtney et al. |
| 2012/0209114 A1 | 8/2012 | Staalsen et al. |
| 2012/0220854 A1 | 8/2012 | Messerly et al. |
| 2012/0245457 A1 | 9/2012 | Crowley |
| 2012/0259209 A1* | 10/2012 | Harhen ............... A61B 8/4254 600/424 |
| 2012/0289830 A1 | 11/2012 | Halmann et al. |
| 2012/0289836 A1 | 11/2012 | Ukimura et al. |
| 2012/0310093 A1 | 12/2012 | Tanabe et al. |
| 2013/0006100 A1 | 1/2013 | Shachar et al. |
| 2013/0006111 A1 | 1/2013 | Sasaki |
| 2013/0009957 A1 | 1/2013 | Arakita |
| 2013/0012820 A1 | 1/2013 | Brown et al. |
| 2013/0018264 A1 | 1/2013 | Gerard et al. |
| 2013/0060116 A1 | 3/2013 | Messerly et al. |
| 2013/0066193 A1 | 3/2013 | Olson et al. |
| 2013/0085416 A1 | 4/2013 | Mest |
| 2013/0102889 A1 | 4/2013 | Southard et al. |
| 2013/0102903 A1 | 4/2013 | Tanaka et al. |
| 2013/0123614 A1 | 5/2013 | Bernstein et al. |
| 2013/0165782 A1 | 6/2013 | Yawata |
| 2013/0165784 A1 | 6/2013 | Kim et al. |
| 2013/0172745 A1 | 7/2013 | Choi |
| 2013/0172747 A1 | 7/2013 | Kim et al. |
| 2013/0172748 A1 | 7/2013 | Kim |
| 2013/0184569 A1 | 7/2013 | Strommer et al. |
| 2013/0197365 A1 | 8/2013 | Baba |
| 2013/0217997 A1 | 8/2013 | Byrd et al. |
| 2013/0237826 A1 | 9/2013 | Levien |
| 2013/0253319 A1 | 9/2013 | Hamilton et al. |
| 2013/0289411 A1 | 10/2013 | Barnard et al. |
| 2013/0296691 A1 | 11/2013 | Ashe |
| 2013/0303886 A1 | 11/2013 | Ludwin et al. |
| 2013/0303915 A1 | 11/2013 | Barnard et al. |
| 2013/0317334 A1 | 11/2013 | Bar-tal et al. |
| 2013/0331697 A1 | 12/2013 | Park et al. |
| 2014/0035914 A1 | 2/2014 | Noshi et al. |
| 2014/0039307 A1 | 2/2014 | Harhen |

(56) References Cited

U.S. PATENT DOCUMENTS

| | | |
|---|---|---|
| 2014/0051984 A1 | 2/2014 | Berger et al. |
| 2014/0107487 A1 | 4/2014 | Kim et al. |
| 2014/0187919 A1 | 7/2014 | Parthasarathy et al. |
| 2014/0187950 A1 | 7/2014 | Torp et al. |
| 2014/0364734 A1 | 12/2014 | Huang |
| 2015/0073266 A1 | 3/2015 | Brannan et al. |
| 2015/0320386 A9 | 11/2015 | Liu |
| 2016/0007842 A1 | 1/2016 | Govari et al. |
| 2016/0331351 A1 | 11/2016 | Guracar |
| 2016/0338675 A1 | 11/2016 | Kubota |

OTHER PUBLICATIONS

R.B. Peterson, J. Hutchins: "The iE33 intelligient echocardiographysystem", MEDICAMUNDI, Nov. 1, 2004 (Nov. 1, 2004), XP002741613, Retrieved from the Internet: http://www.healthcare.philips.com/pwc_hc/main/about/assets/Docs/medicamundi/mm_vol148_no3/11_Petrson.pdf, retrieved on Jun. 30, 2015.

\* cited by examiner

ULTRASOUND IMAGING SYSTEM HAVING AUTOMATIC IMAGE PRESENTATION

CROSS-REFERENCE TO RELATED APPLICATIONS

This application is a U.S. national phase of International Application No. PCT/US2015/018068, filed Feb. 27, 2015, which claims priority to U.S. provisional patent application Ser. No. 62/081,275, filed Nov. 18, 2014, which is incorporated herein by reference in its entirety.

BACKGROUND OF THE INVENTION

1. Field of the Invention

The present invention relates to ultrasound imaging, and, more particularly, to an ultrasound imaging system that assists in the positioning of an ultrasound probe.

2. Description of the Related Art

Correctly positioning an ultrasound probe such that a diagnostically relevant image is produced is a skill often only obtained after training and consistent ultrasound use. This initial "training period" necessary to become proficient in ultrasound imaging may be a contributing factor to the current underutilization of ultrasound by non-sonographers.

What is needed in the art is an ultrasound imaging system, as in the present invention, which assists a person not experienced in ultrasound imaging in successful image acquisition, via system assisted positioning of an ultrasound probe, such that an image of a location of interest under, i.e., in the imaging view of, the ultrasound probe can be displayed.

SUMMARY OF THE INVENTION

The present invention provides an ultrasound imaging system that assists in image acquisition, and in positioning of an ultrasound probe, such that an image of a location of interest under, i.e., in the imaging view of, the probe can be displayed. For example, the ultrasound imaging system assists in the positioning of an ultrasound probe such that a specific image containing a medical device and/or the surrounding area can automatically be presented to the user. The system may further be used to create three-dimensional (3D) images of underlying structures, which may convey additional information regarding the state of the underlying anatomy. This may assist one performing peripheral arterial disease (PAD) or other interventional procedures.

The invention in one form is directed to an ultrasound imaging system that includes an electromagnetic (EM) field generator configured to generate an EM locator field. An interventional medical device is defined by an elongate body having a distal tip and a distal end portion extending proximally from the distal tip. The interventional medical device has a first tracking element mounted at the distal end portion of the interventional medical device. The first tracking element is configured to generate tip location data based on the EM locator field. An ultrasound probe has a probe housing, an ultrasound transducer mechanism, and a second tracking element. The probe housing has a handle portion and a head portion. The ultrasound transducer mechanism and the second tracking element are mounted to the probe housing. The ultrasound transducer mechanism has an active ultrasound transducer array configured to generate two-dimensional ultrasound slice data at any of a plurality of discrete imaging locations within a three-dimensional imaging volume associated with the head portion. The second tracking element is configured to generate probe location data based on the EM locator field. A display screen is configured to display an ultrasound image. A processor circuit is communicatively coupled to the first tracking element, the second tracking element, the ultrasound transducer mechanism, and the display screen. The processor circuit is configured to execute program instructions to process the two-dimensional ultrasound slice data to generate the ultrasound image for display at the display screen. Also, the processor circuit is configured to generate a positioning signal based on the tip location data and the probe location data to dynamically position the active ultrasound transducer array at a desired imaging location of the plurality of discrete imaging locations so that the two-dimensional ultrasound slice data includes at least the distal tip of the interventional medical device so long as a location of the distal tip of the interventional medical device remains in the three-dimensional imaging volume.

A further version of the invention lies in the electromagnetic field generator adapted for use in such a system, the interventional medical device adapted for use in such a system, an ultrasound probe adapted for use in such a system, a display screen adapted for use in such a system, and a processor circuit adapted for use in such a system. An alternative version of the invention lies in a system comprising a combination of any of the objects recited in the previous sentence.

The invention in another form is directed to a method of operating an ultrasound imaging system, including acquiring a position of a first tracking element associated with an interventional medical device; acquiring a position of a second tracking element associated with an ultrasound probe; determining an ultrasound imaging plane position of the ultrasound probe based on the position of the second tracking element; determining an offset distance between the position of first tracking element of the interventional medical device and the ultrasound plane position; and driving an ultrasound transducer mechanism to position an active ultrasound transducer array of the ultrasound probe at a determined point of convergence as defined by the offset distance.

In accordance with another aspect of the invention, a motion indicator is located on at least one of the ultrasound probe and the display screen. The processor circuit is operably coupled to the motion indicator, wherein if the distal tip of the interventional medical device is presently located outside the three-dimensional imaging volume, a visual prompt is generated at the motion indicator to prompt the user to move the head portion of the ultrasound probe in a particular direction to a general location such that the distal tip of the interventional medical device resides in the three-dimensional imaging volume.

In accordance with another aspect of the invention, a third tracking element is attached to a patient, wherein when the third tracking element is energized by the EM field generator. The third tracking element generates six axis patient location data, which is supplied to the processor circuit. The processor circuit processes the six-axis patient location data and assigns location information for images captured by the active ultrasound transducer array to known positions within a 3D volume referenced from the third tracking element.

In accordance with another aspect of the invention, the ultrasound imaging system has a three-dimensional imaging mode, wherein with the ultrasound probe held in a fixed position over an area of interest, a scanning signal is supplied to the ultrasound transducer mechanism to scan the active ultrasound transducer array over at least a portion of the possible imaging volume located below the transducer array. The active transducer array is repeatedly actuated during the scan to generate a plurality of sequential two-dimensional ultrasound data slices which are combined to form three-dimensional ultrasound volumetric data from which a three-dimensional ultrasound image is generated.

In accordance with another aspect of the invention, the active ultrasound transducer array is operated to generate multiple sets of ultrasound image data that includes metadata describing the location of the scan within the three-dimensional volume. The multiple sets of ultrasound image data are summed to generate composite ultrasound image data.

In accordance with another aspect of the invention, a desired image plane is defined in the three-dimensional ultrasound volumetric data. At least one synthetic scan plane is generated corresponding to the desired image plane.

In accordance with another aspect of the invention, a first two-dimensional ultrasound image slice is generated from a series of two-dimensional B-scan ultrasound image slices acquired from the three-dimensional ultrasound volumetric data. The first two-dimensional ultrasound image slice includes a particular region of interest. The first two-dimensional ultrasound image slice lies in a first imaging plane different from that of the native B-scan imaging plane of the series of two-dimensional ultrasound image slices. At least one slice selection slider provides a sequential parallel variation from the first two-dimensional ultrasound image slice to manually select a second two-dimensional ultrasound image slice parallel to the first two-dimensional ultrasound image, wherein the second two-dimensional ultrasound image slice lies on either side of the first two-dimensional ultrasound image slice.

In accordance with another aspect of the invention, an orientation of the ultrasound image that is displayed on a display screen is adjusted such that a vertical top of the acquired ultrasound image data is always rendered as "up" on the display screen relative to the position of the patient, and regardless of the actual orientation of ultrasound probe relative to the patient.

Another aspect of the invention is directed to a method of operating an ultrasound imaging system, including acquiring a position of a first tracking element associated with an interventional medical device; acquiring a position of a second tracking element associated with an ultrasound probe; determining an ultrasound imaging plane position of the ultrasound probe based on the position of the second tracking element; determining an offset distance between the position of first tracking element of the interventional medical device and the ultrasound plane position; and using the offset distance to dynamically control at least one ultrasound imaging setting of the ultrasound imaging system in near real time. As used herein, the term "near real time" means real time as limited by data acquisition and processing speed of the processing system. The at least one ultrasound imaging setting may include ultrasound focus, such that a lateral resolution is optimized at a depth that contains the interventional medical device. Also, the at least one ultrasound imaging setting may include a depth setting, such that a depth of imaging is automatically adjusted to match a depth of the interventional medical device. Also, the at least one ultrasound imaging setting may include zoom, wherein an imaging window can be "zoomed" such that a larger view of an area of interest is automatically displayed to the user.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
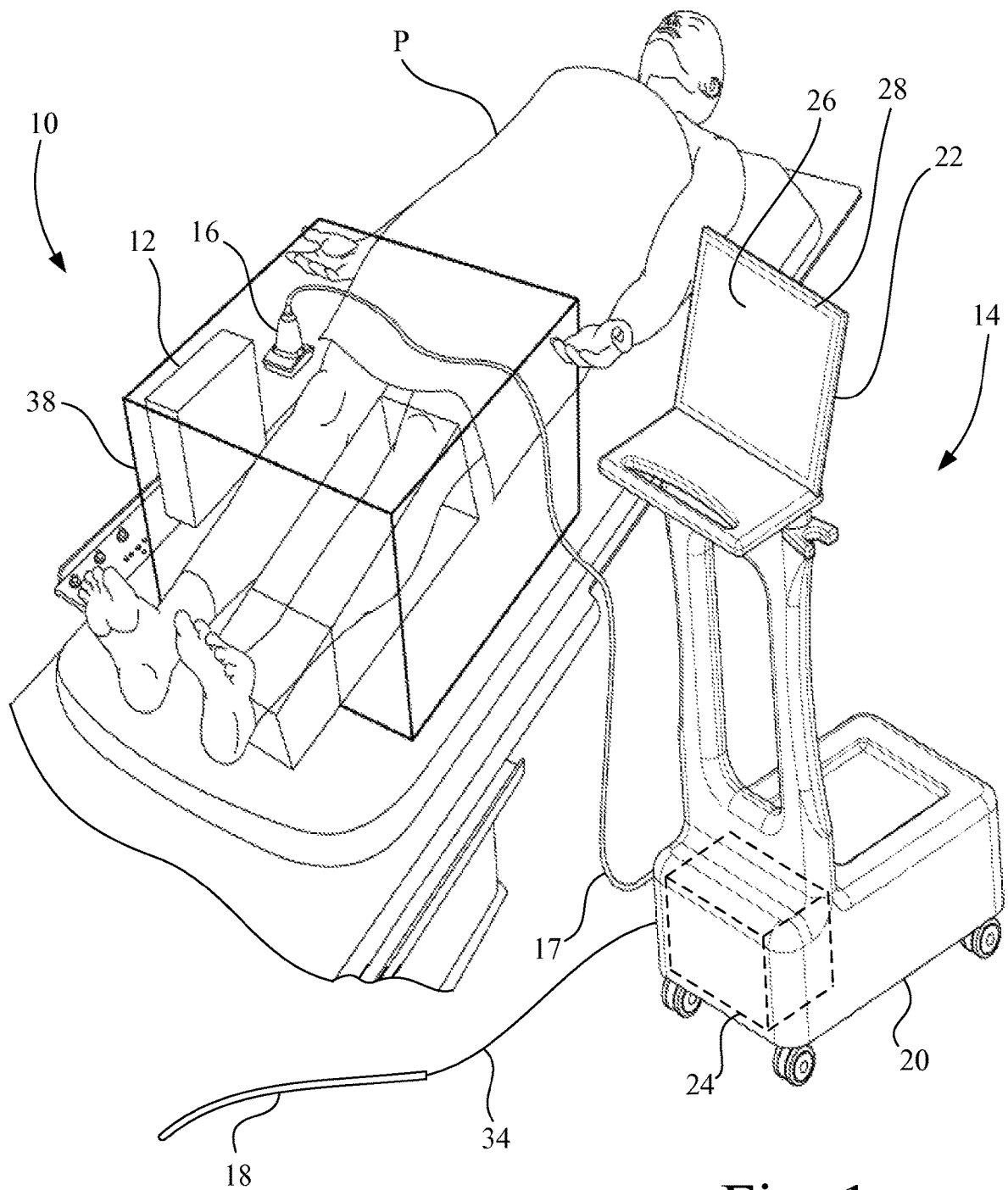
FIG. 1 is an illustration of an ultrasound imaging system in accordance with an aspect of the present invention.
Figure 2:
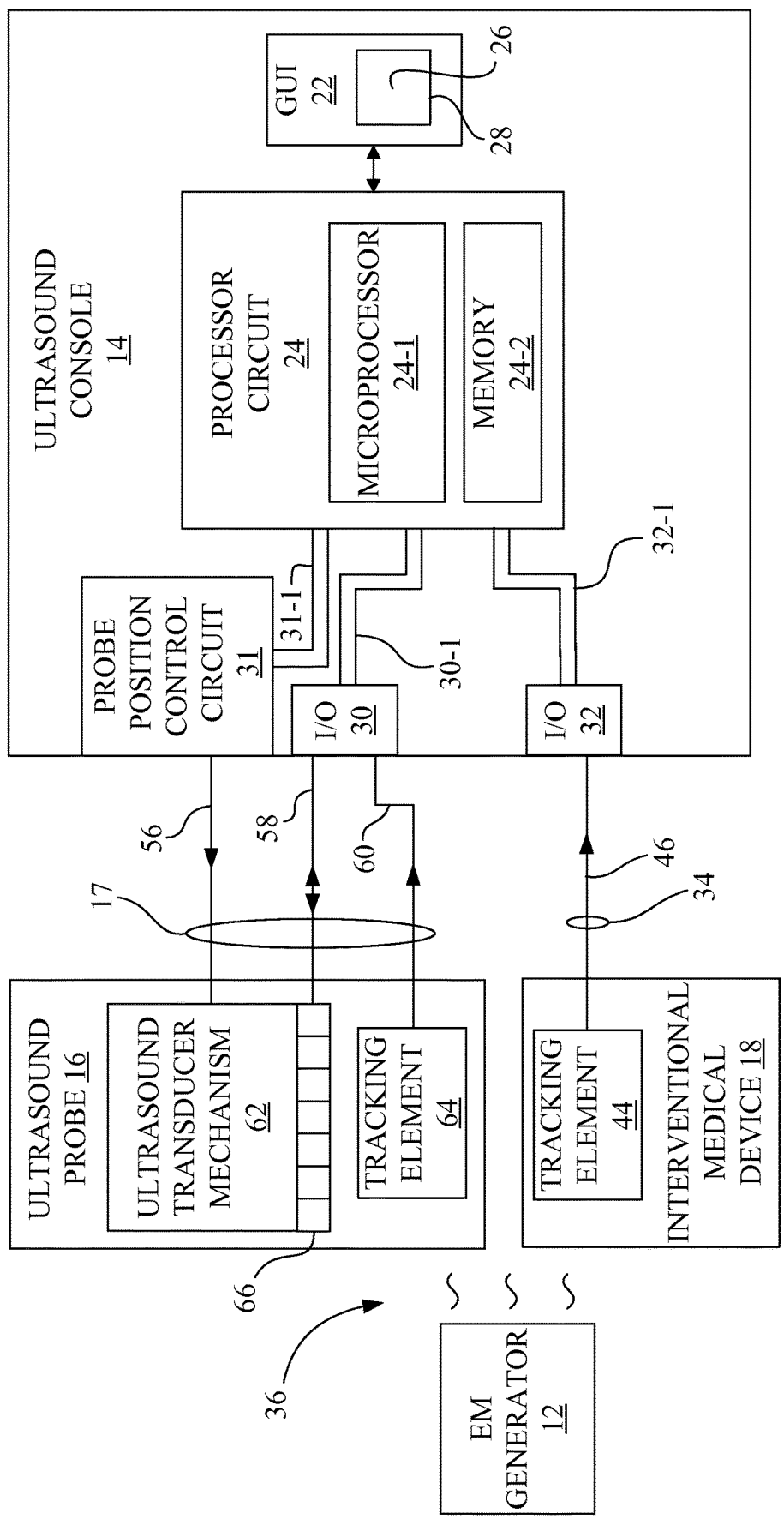
FIG. 2 is an electrical block diagram of the ultrasound imaging system of FIG. 1.

Referring now to the drawings, and more particularly to FIGS. 1 and 2, there is shown an ultrasound imaging system 10 in accordance with the present invention.

Ultrasound imaging system 10 includes an electromagnetic (EM) field generator 12, an ultrasound console 14, and an ultrasound probe 16 (handheld). Ultrasound probe 16 is connected to an ultrasound console 14 by a flexible electrical cable 17. Supplemental to ultrasound imaging system 10 is an interventional medical device 18.

As used herein, the term "interventional medical device" is an elongate intrusive medical device that is configured to be inserted into the tissue, vessel or cavity of a patient. In the context of the present invention, interventional medical device 18 may be, for example, a catheter, a lesion crossing catheter such as the CROSSER® Catheter available from C. R. Bard, Inc., a guide wire, a sheath, an angioplasty balloon, a stent delivery catheter, or a needle. It is intended that the interventional medical device 18 may be considered as a part of the overall ultrasound imaging system 10, but alternatively, also may be considered as an auxiliary part of ultrasound imaging system 10 as a separately provided item.

Ultrasound imaging system 10 is configured to track the location of the ultrasound probe 16 and interventional medical device 18, and in turn, to operate ultrasound probe 16 such that an active ultrasound transducer array of ultrasound probe 16 is dynamically positioned to image a desired portion of interventional medical device 18, as further described below.

In the present embodiment, ultrasound console 14 includes a mobile housing 20, to which is mounted a graphical user interface 22, and a processor circuit 24. Graphical user interface 22 may be in the form of a touch-screen display 26 having a display screen 28. Graphical user interface 22 is used in displaying information to the user, and accommodates user input via the touch-screen 26. For example, touch-screen 26 is configured to display an ultrasound image formed from two-dimensional ultrasound slice data provided by ultrasound probe 16, to display virtual location information of tracked elements within a 3D volume, and to display prompts intended to guide the user in the correct positioning of the ultrasound probe 16 above the area of interest.

Processor circuit 24 is an electrical circuit that has data processing capability and command generating capability, and in the present embodiment has a microprocessor 24-1 and associated non-transitory electronic memory 24-2. Microprocessor 24-1 and associated non-transitory electronic memory 24-2 are commercially available components, as will be recognized by one skilled in the art. Microprocessor 24-1 may be in the form of a single microprocessor, or two or more parallel microprocessors, as is known in the art. Non-transitory electronic memory 24-2 may include multiple types of digital data memory, such as random access memory (RAM), non-volatile RAM (NVRAM), read only memory (ROM), and/or electrically erasable programmable read-only memory (EEPROM). Non-transitory electronic memory 24-2 may further include mass data storage in one or more of the electronic memory forms described above, or on a computer hard disk drive or optical disk. Alternatively, processor circuit 24 may be assembled as one or more Application Specific Integrated Circuits (ASIC).

Processor circuit 24 processes program instructions received from a program source, such as software or firmware, to which processor circuit 24 has electronic access. More particularly, processor circuit 24 is configured, as more fully described below, to process location signals received from ultrasound probe 16 and interventional medical device 18, and to generate a digital positioning signal that is conditioned and provided as a control output to ultrasound probe 16. More particularly, the digital positioning signal and control output correspond to a coordinate in the scan axis, e.g., the y-axis, of ultrasound probe 16 where the active ultrasound transducer array of ultrasound probe 16 is to be positioned.

Processor circuit 24 is communicatively coupled to a probe input/output (I/O) interface circuit 30, a probe position control circuit 31, and a device input/output (I/O) interface circuit 32 via an internal bus structure 30-1, 31-1, and 32-1, respectively. As used herein, the term "communicatively coupled" means connected for communication over a communication medium, wherein the communication medium may be a direct wired connection having electrical conductors and/or printed circuit electrical conduction paths, or a wireless connection, and may be an indirect wired or wireless connection having intervening electrical circuits, such as amplifiers or repeaters. Probe input/output (I/O) interface circuit 30 and probe position control circuit 31 are configured to connect to electrical cable 17, which in turn is connected to ultrasound probe 16. In the present embodiment, device input/output (I/O) interface circuit 32 is configured to connect to a flexible electrical cable 34, which in turn is connected to interventional medical device 18.

Referring again to FIG. 1, EM field generator 12 is placed near the area of interest of the patient P, and is used in triangulating the location of one or more tracked elements, such as the position of ultrasound probe 16 and interventional medical device 18. EM field generator 12 may be, for example, the field generator of an Aurora® Electromagnetic Tracking System available from Northern Digital Inc. (NDI), which generates a base electromagnetic field that radiates in a known orientation to facilitate electromagnetic spatial measurement, which will be referred to hereinafter as an EM locator field 36 (see FIG. 2). The field strength of the EM locator field 36 defines a detection volume 38, as diagrammatically illustrated as a cube volume, for convenience, in FIG. 1.

Figure 3:
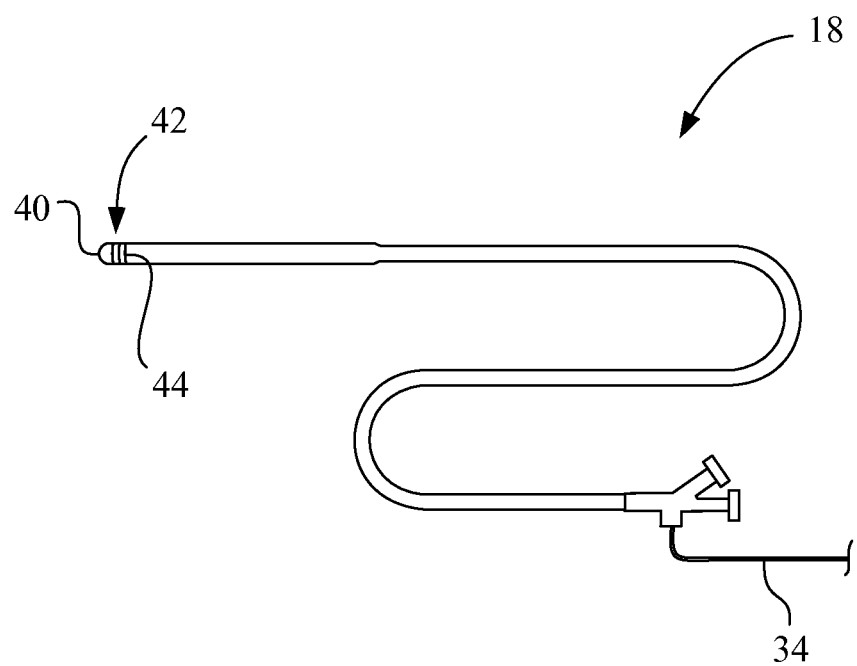
FIG. 3 shows an interventional medical device, such as a catheter or sheath, having a tracking element near its distal tip.

Referring also to FIG. 3, interventional medical device 18 has a distal tip 40 and a distal end portion 42 extending proximally from the distal tip 40. In the present embodiment, a tracking element 44 (i.e., a wire electrical tracking coil) is mounted at distal end portion 42 of interventional medical device 18 near distal tip 40. In the context of the preceding sentence, the term "near" is a range of zero to 2 centimeters (cm), and the extent of distal end portion 42 is in a range of 1 millimeter (mm) to 3 cm. Those skilled in the art will recognize, however, that the exact location of the placement of tracking element 44 on interventional medical device 18 will depend on the portion of interventional medical device 18 that is to be tracked by ultrasound imaging system 10. Tracking element 44 allows the location of interventional medical device 18 to be known relative to ultrasound probe 16, as more fully described below.

Tracking element 44 is configured to generate tip location data defining five degrees of freedom based on the EM locator field 36 generated by EM field generator 12. The five degrees of freedom are the X-axis, Y-axis, Z-axis, pitch, and yaw. A sixth degree of freedom, i.e., roll, may be also included, if desired. Tracking element 44 of interventional medical device 18 is communicatively coupled to processor circuit 24 of ultrasound console 14 via electrical cable 34, serving as a communication link 46 between processor circuit 24 and tracking element 44. As used herein, "communications link" refers to an electrical transmission of data, i.e., information, and/or electrical power signals, over a wired or wireless communication medium. In the present embodiment, the communication link 46 provided by electrical cable 34 is a multi-conductor electrical cable that physically connects tracking element 44 to the ultrasound console 14, and in turn to processor circuit 24.

Figure 4:
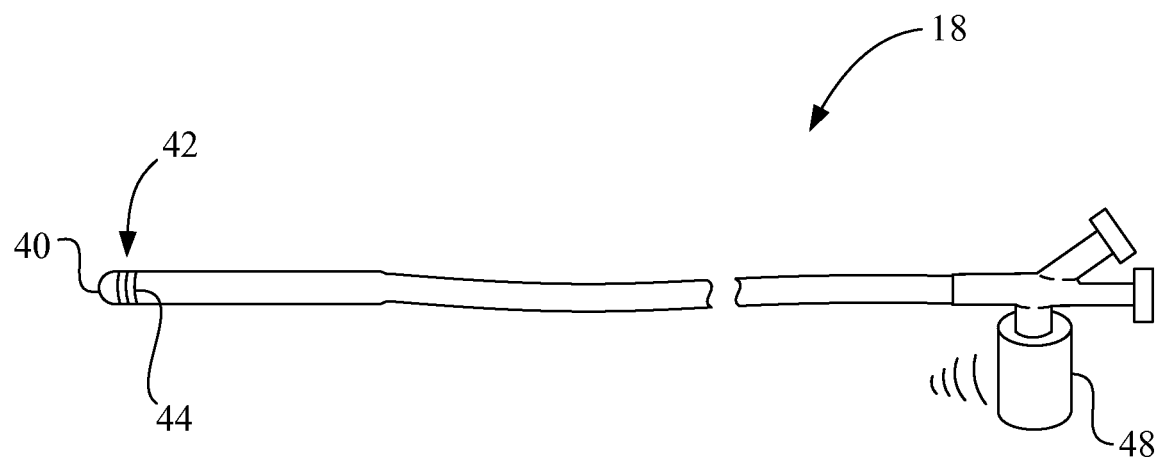
FIG. 4 shows an interventional medical device, such as a catheter, having a wireless dongle.

Alternatively, as depicted in FIG. 4, in place of a physical connection, communication link 46 may be in the form of a short range wireless connection, such as Bluetooth, via a Bluetooth dongle 48 attached to interventional medical device 18. The Bluetooth dongle 48 is configured as a Bluetooth transmitter using Bluetooth protocol, and a corresponding Bluetooth receiver is connected to processor circuit 24. Bluetooth dongle 48 communicates tracking information from tracking element 44, and other information associated with interventional medical device 18, such as an operating state, to processor circuit 24 of ultrasound imaging system 10. Also, Bluetooth dongle 48 may be used to provide power to the EM tracking components incorporated into interventional medical device 18, in the case where the EM tracking component is an active circuit requiring a power source.

Bluetooth dongle 48 may be disposable, and included with each interventional medical device 18. Alternatively, Bluetooth dongle 48 may be reusable. Sterility requirements for the reusable dongle are addressed by placing the sterilized dongle in a sterile bag through which a sterile connection to interventional medical device 18 is made.

Figure 5A:
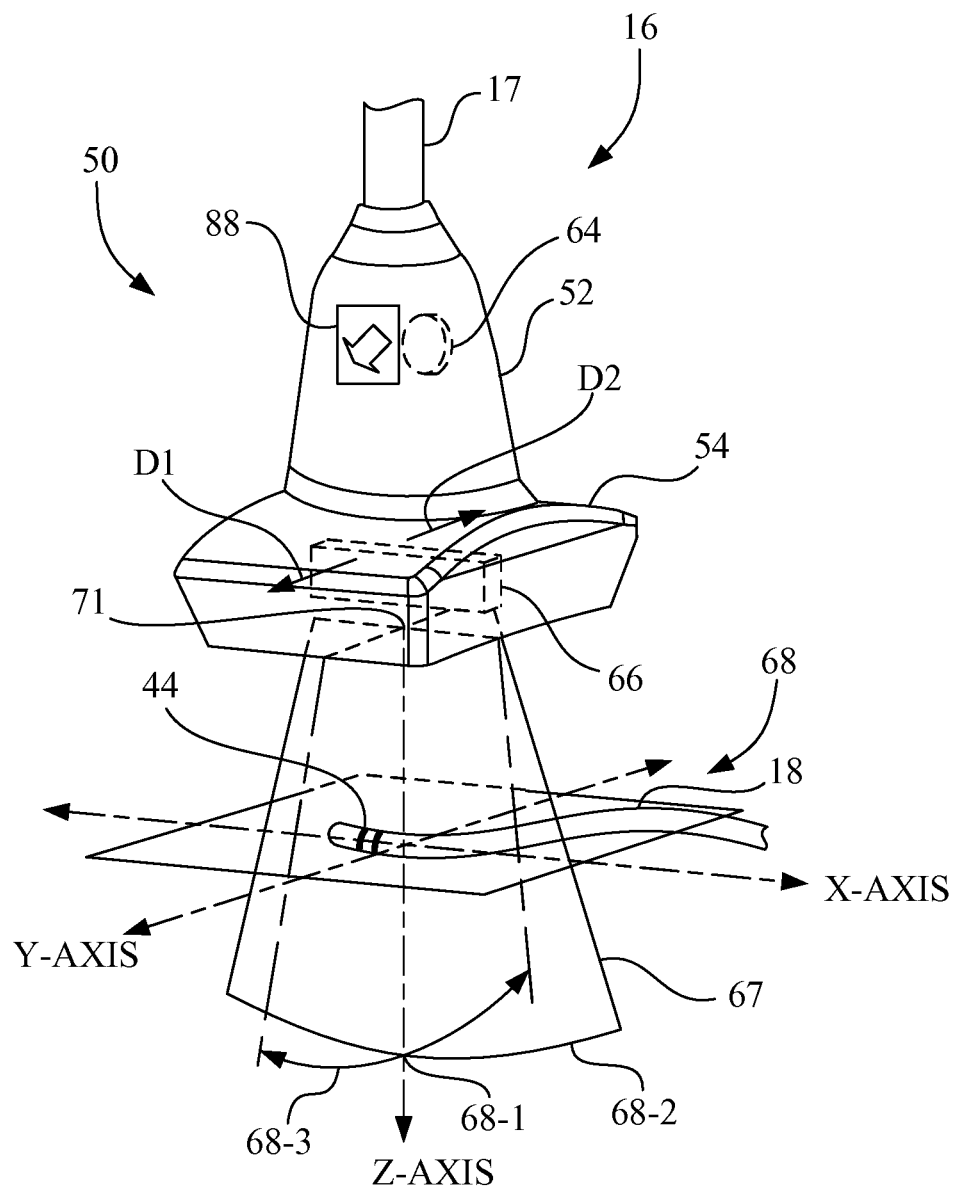
FIG. 5A shows the ultrasound probe of FIG. 1 having an ultrasound transducer mechanism with an active ultrasound transducer array configured to generate two-dimensional ultrasound slice data.

As shown in FIG. 5A, ultrasound probe 16 includes a probe housing 50 having a handle portion 52 joined with a head portion 54. In the present embodiment, handle portion 52 has an extent that is generally perpendicular (range of ±5 degrees) to the extent of head portion 54.

Ultrasound probe 16 is communicatively coupled to processor circuit 24 of ultrasound console 14 via electrical cable 17, which may be a wired or a wireless connection. In the present embodiment, with reference to FIG. 2, electrical cable 17 is depicted as a multi-conductor electrical cable that physically connects ultrasound probe 16 to ultrasound console 14, and includes a communication link 56, a communication link 58, and a communication link 60, each formed with wire conductors. However, it is contemplated that one or more of communication link 56, communication link 58, and communication link 60 may be in the form of a (short range) wireless connection, such as Bluetooth. Portions of the processor circuit 24 could also be embedded in the ultrasound probe to analyze or process the received/transmitted signal to the ultrasound emitting element. The analyzed or processed signal is then transmitted back to the console via electrical cable.

Referring to FIG. 2, ultrasound probe 16 includes an ultrasound transducer mechanism 62 and a tracking element 64. Both ultrasound transducer mechanism 62 and tracking element 64 are mounted to probe housing 50 (see also FIG. 5A), and may be contained within probe housing 50, which may be formed from plastic. Also, tracking element 64 may be embedded in the plastic of probe housing 50. Ultrasound transducer mechanism 62 is communicatively coupled to processor circuit 24 via communication links 56 and 58.

Referring to FIGS. 2 and 5A, ultrasound transducer mechanism 62 has an active ultrasound transducer array 66 configured to generate two-dimensional ultrasound slice data representing a two-dimensional ultrasound imaging slice 67 at any of a plurality of discrete imaging locations within a three-dimensional imaging volume 68 associated with head portion 54 of ultrasound probe 16. The three-dimensional imaging volume 68 is defined by a depth 68-1 of penetration of the ultrasound emission in the direction of the z-axis, a width 68-2 of ultrasound emission in the x-axis, and an ultrasound transducer scan extent 68-3 along the y-axis. Active ultrasound transducer array 66 may be, for example, a one-dimensional transducer array in the form of a linear ultrasound transducer array, or alternatively, may be in the form of a convex or concave ultrasound transducer array. As used herein, the term "one-dimensional transducer array" is an array of ultrasound transducer elements arranged in a single row, wherein the row may be linear or curved.

Active ultrasound transducer array 66 is communicatively coupled to processor circuit 24 via communication link 58, and supplies two-dimensional ultrasound data to processor circuit 24 via communication link 58. Automatically, or alternatively based on a user input at graphical user interface 22, processor circuit 24 executes program instructions to store the two-dimensional ultrasound data in mass storage provided in non-transitory electronic memory 24-2.

Figure 5B:
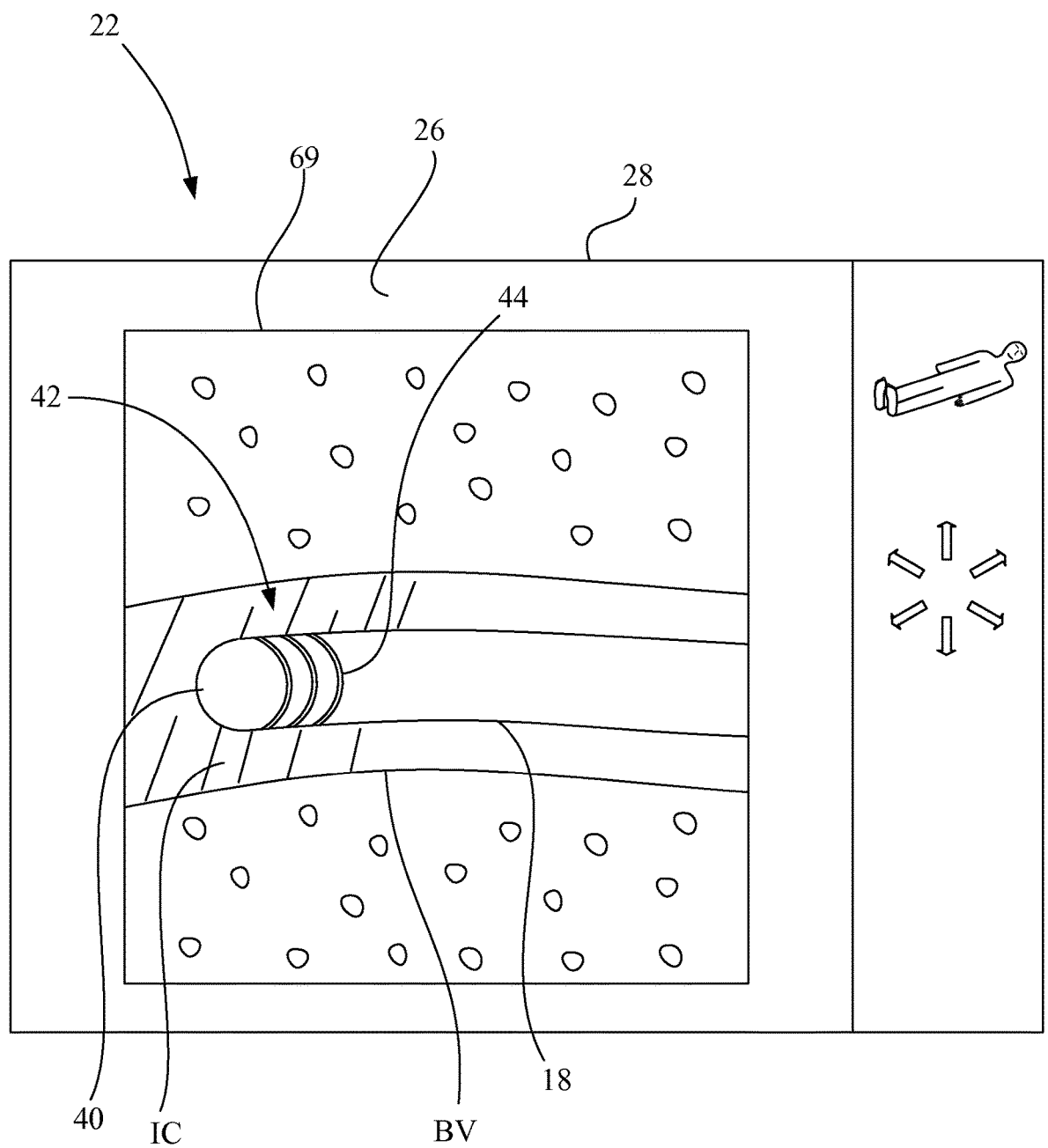
FIG. 5B shows a graphical user interface having a display screen showing a two-dimensional ultrasound image of the two-dimensional ultrasound slice data acquired by the ultrasound probe depicted in FIG. 5A.

Referring also to FIG. 5B, processor circuit 24 includes circuitry, or alternatively executes program instructions, to convert the two-dimensional ultrasound data to a form for viewing as a two-dimensional ultrasound image 69 on display screen 28 of graphical user interface 22. The two-dimensional ultrasound image 69 depicts interventional medical device 18 having tracking element 44 located in a blood vessel BV, and depicts distal tip 40 of distal end portion 42 of interventional medical device 18 engaged with an intravascular occlusion IC.

Referring again to FIGS. 2 and 5A, tracking element 64 (i.e., a wire electrical tracking coil) is configured to generate probe location data defining six degrees of freedom based on the EM locator field 36 generated by EM field generator 12. The six degrees of freedom are the X-axis, Y-axis, Z-axis, pitch, yaw, and roll. Tracking element 64 is communicatively coupled to processor circuit 24 via communication link 60, and supplies probe location data to processor circuit 24 via communication link 60. Tracking element 64 allows for the determination of the location of ultrasound probe 16 within detection volume 38 as depicted in FIG. 1, wherein detection volume 38 is considerably larger (more than 20 times larger) than the three-dimensional imaging volume 68 of ultrasound probe 16 depicted in FIG. 5A.

Figure 6A:
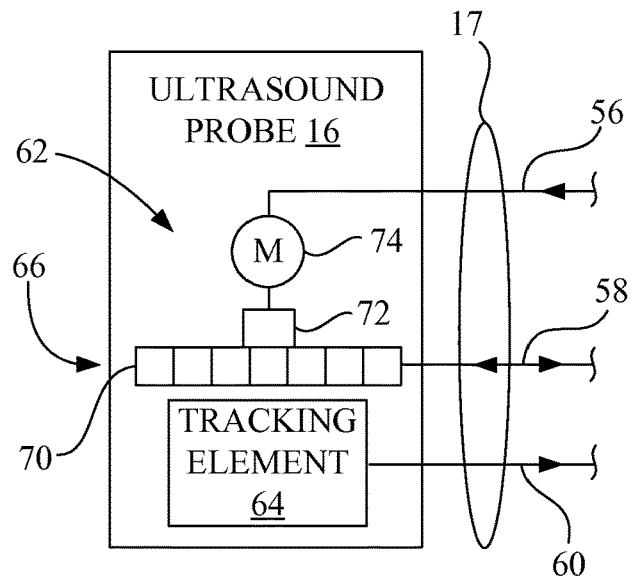
FIG. 6A is a block diagram of an embodiment of the ultrasound probe of FIG. 1, having a movable one-dimensional transducer array.
Figure 6B:
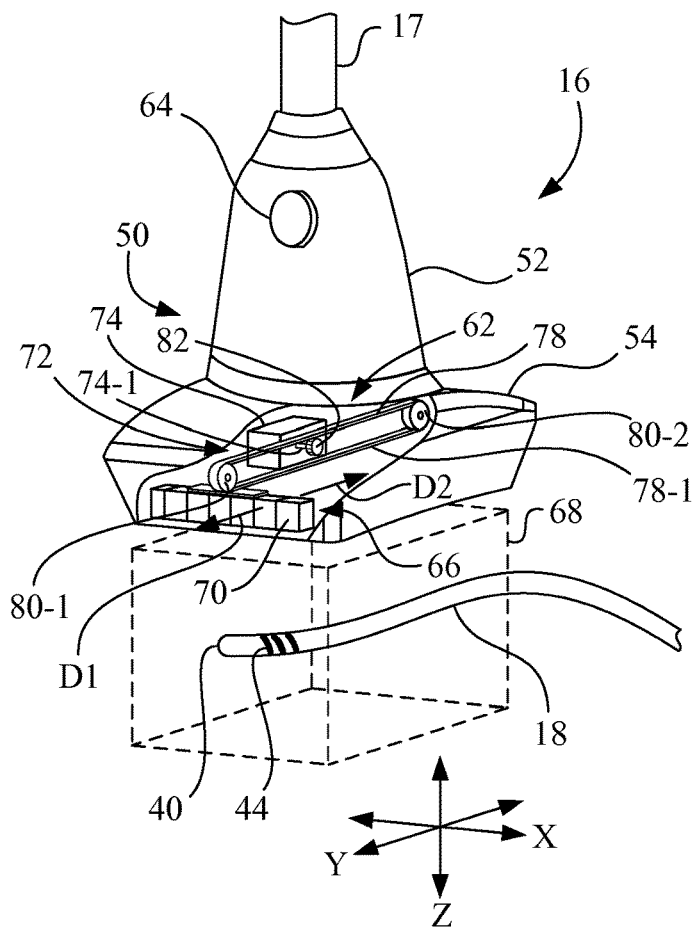
FIG. 6B shows the ultrasound probe of FIGS. 1 and 6A, with a portion broken away to expose an ultrasound transducer mechanism having a movable one-dimensional transducer array, a carriage, and a stepper motor.
Figure 7A:
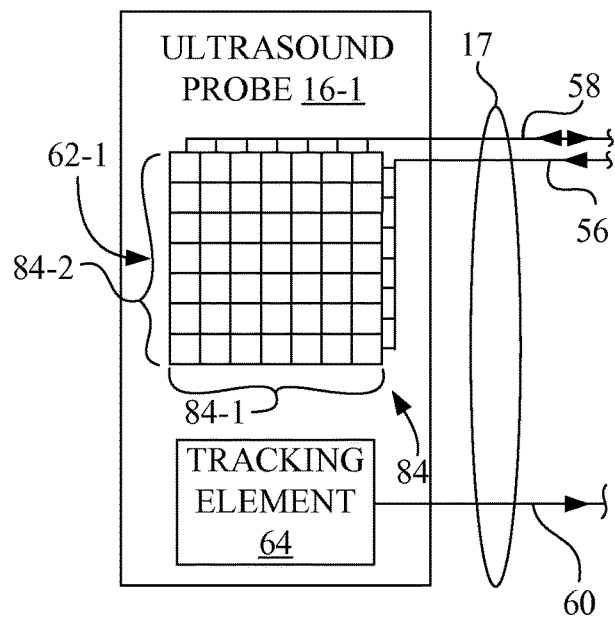
FIG. 7A is a block diagram of another embodiment of the ultrasound probe of FIG. 1, having a stationary two-dimensional transducer array.
Figure 7B:
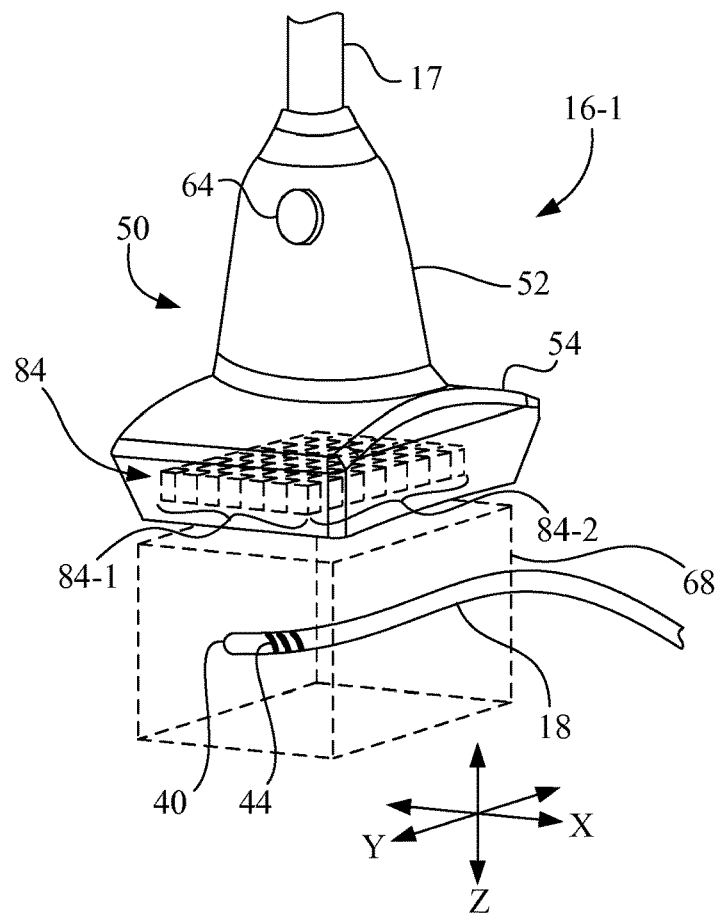
FIG. 7B shows the ultrasound probe of FIG. 7A, depicting the two-dimensional transducer array in phantom (dashed) lines.

In accordance with the present invention, active ultrasound transducer array 66 of ultrasound transducer mechanism 62 of ultrasound probe 16 may incorporate a movable one-dimensional (1D) transducer array, as in the embodiment depicted in FIGS. 6A and 6B. Alternatively, as depicted in FIGS. 7A and 7B, active ultrasound transducer array 66 of ultrasound transducer mechanism 62 of ultrasound probe 16 may be in the form of a selectable portion of a two-dimensional (2D) matrix transducer array.

In the embodiment depicted in FIGS. 6A and 6B, active ultrasound transducer array 66 is physically movable relative to the probe housing 50, i.e., is dynamically positioned within probe housing 50, in order to capture ultrasound images of locations within the three-dimensional imaging volume 68 (diagrammatically illustrated cube volume, for convenience) beneath ultrasound probe 16.

In the embodiment of FIGS. 6A and 6B, ultrasound transducer mechanism 62 includes a one-dimensional (1D) ultrasound transducer array 70, a carriage 72, and a stepper motor 74. In the present embodiment, one-dimensional ultrasound transducer array 70 serves as the active ultrasound transducer array 66. The one-dimensional ultrasound transducer array 70 has a row of a plurality of discrete ultrasound transducer elements.

Carriage 72 is connected to one-dimensional ultrasound transducer array 70, such that one-dimensional ultrasound transducer array 70 moves in unison with carriage 72. Carriage 72 converts a rotation of a rotatable shaft 74-1 of stepper motor 74 into a linear translation of carriage 72, and in turn, into a linear translation of one-dimensional ultrasound transducer array 70 relative to head portion 54 of probe housing 50, in a determined one of two translation directions D1, D2.

Stepper motor 74 is operably connected (electrically and communicatively) to probe position control circuit 31 (see FIG. 2) via communication link 56 of electrical cable 17. In the present embodiment, probe position control circuit 31 is in the form of a motor control circuit, which converts the digital positioning signal supplied by processor circuit 24 into a stepper motor positioning signal, which may include multiple stepper motor control signals, and which are supplied by motor control circuit 76 to stepper motor 74 to command rotation of rotatable shaft 74-1 by an amount corresponding to the amount and position dictated by the digital positioning signal. In the present embodiment, the digital positioning signal and the stepper motor positioning signal may be referred to herein collectively as the "positioning signal", since the stepper motor positioning signal is a form change of the digital positioning signal, and the "positioning signal" is considered herein to have been generated by processor circuit 24.

Carriage 72 converts the rotation of rotatable shaft 74-1 of stepper motor 74 into a linear translation of carriage 72, and in turn, moves one-dimensional ultrasound transducer array 70 relative to head portion 54 of probe housing 50 in a determined one of two translation directions D1, D2, to a location thus dictated by the digital positioning signal generated by processor circuit 24. Thus, based on the positioning signal initiated by processor circuit 24, the one-dimensional ultrasound transducer array 70 may be moved to a desired position relative to head portion 54 of probe housing 50.

FIG. 6B shows an embodiment of carriage 72, wherein carriage 72 has an endless toothed belt 78 suspended between two longitudinally spaced idler gears/pulleys 80-1, 80-2. Rotatable shaft 74-1 of stepper motor 74 is connected to a drive gear 82. Drive gear 82 is drivably engaged with the teeth of endless toothed belt 78. One-dimensional ultrasound transducer array 70 is attached to the lower run 78-1 of endless toothed belt 78, and is movable along the longitudinal extent between the two longitudinally spaced idler gears/pulleys 80-1, 80-2. As such, the arrangement of toothed belt 78 suspended between two longitudinally spaced idler gears/pulleys 80-1, 80-2 converts a rotation of the rotatable shaft 74-1 of the stepper motor 74 into a translation of the one-dimensional ultrasound transducer array 70 in a selectable one of the two translation directions D1, D2.

In the alternative embodiment depicted in FIGS. 7A and 7B, and identified as ultrasound probe 16-1, an alternative ultrasound transducer mechanism 62-1 includes a two-dimensional (2D) ultrasound transducer array 84, and probe position control circuit 31 (see FIG. 2) is in the form of a matrix address circuit of the type used in addressing electronic memory. Two-dimensional ultrasound transducer array 84 has a plurality of columns 84-1 and a plurality of addressable rows 84-2 of discrete ultrasound transducer elements arranged in a matrix pattern. The two-dimensional ultrasound transducer array 84 may be a planar transducer arrangement, or alternatively may be a concave or convex arrangement. Two-dimensional ultrasound transducer array 84 is communicatively coupled to processor circuit 24 via communications link 58 to supply two-dimensional ultrasound data from two-dimensional ultrasound transducer array 84 to processor circuit 24.

In the embodiment of FIGS. 7A, 7B, with reference to FIG. 2, probe position control circuit 31 is electrically connected to processor circuit 24 to receive the digital positioning signal generated by processor circuit 24. In the present embodiment, probe position control circuit 31 operates as a matrix address circuit to convert the digital positioning signal supplied by processor circuit 24 into a row selection positioning signal which is supplied to two-dimensional (2D) ultrasound transducer array 84 via communications link 56 to dynamically select one row of the plurality of rows 84-2 of discrete ultrasound transducer elements as the active linear ultrasound transducer array 66. Thus, the row selection positioning signal corresponds to the position dictated by the digital positioning signal generated by processor circuit 24.

In the embodiment of FIGS. 7A and 7B, since the row selection positioning signal is a form change of the digital positioning signal, the digital positioning signal and the row selection positioning signal may be referred to herein collectively as the "positioning signal", and the "positioning signal" is considered herein to have been generated by processor circuit 24.

As such, the embodiment of FIGS. 7A and 7B emulates the dynamic positioning of the one-dimensional ultrasound transducer array 70 discussed above with respect to FIGS.

6A and 6B, and allows for similar control of where the ultrasound probe will image within the three-dimensional imaging volume 68 beneath the ultrasound probe (see FIG. 5A).

In accordance with the present invention, and in view of the embodiments discussed above, ultrasound imaging system 10 provides a "lock-on" functionality, wherein the position of each of the ultrasound probe 16 and interventional medical device 18 are tracked, and the active ultrasound transducer array 66 in ultrasound probe 16 is dynamically positioned at a convergence of the tracking information, which is further described with reference to the flowchart of FIG. 8. Recall that processor circuit 24 is communicatively coupled to each of the tracking element 44 of interventional medical device 18, tracking element 64 of ultrasound probe 16, ultrasound transducer mechanism 62 of ultrasound probe 16, and to the graphical user interface 22 having display screen 28.

Figure 8:
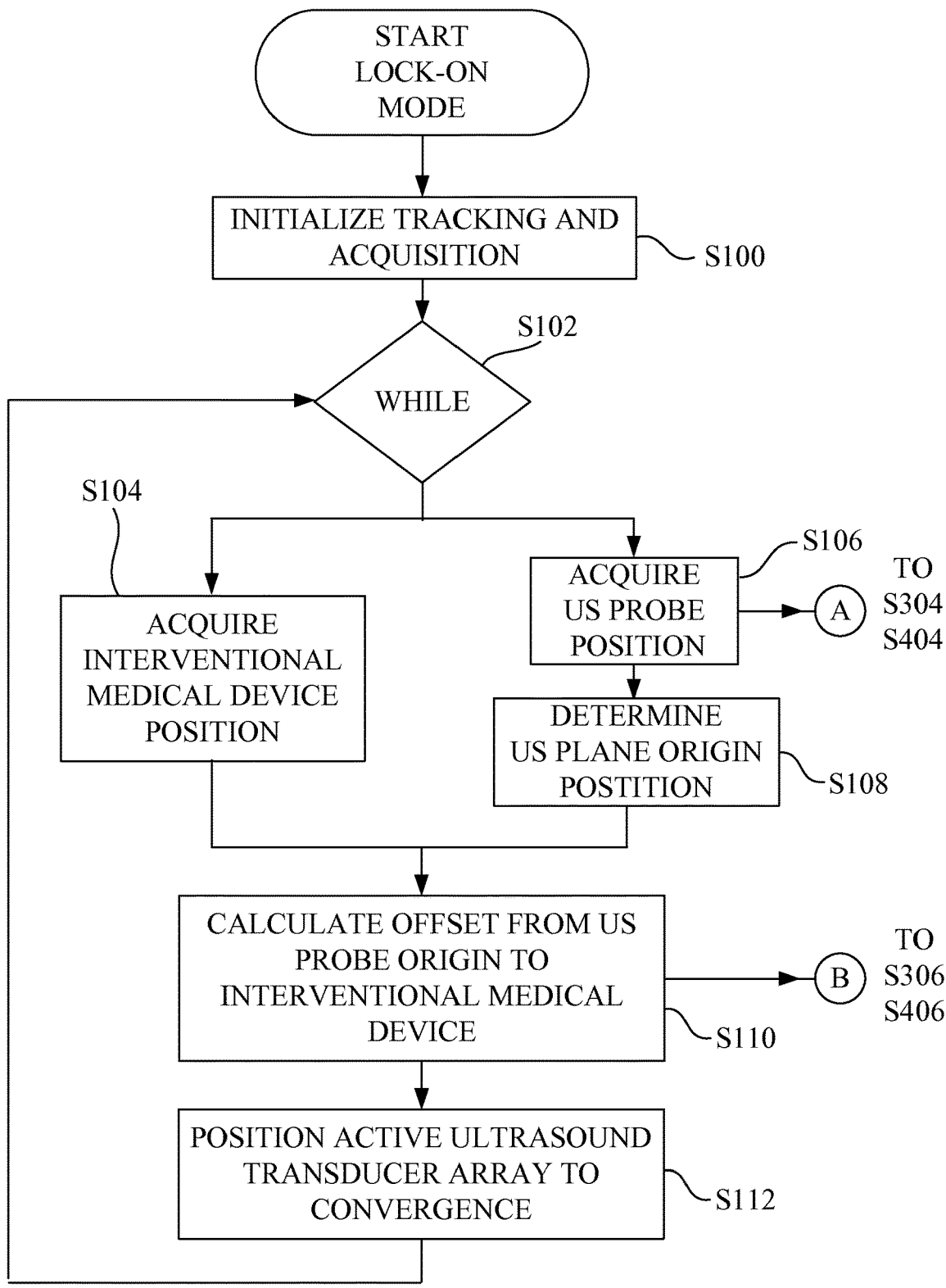
FIG. 8 is a flowchart depicting a lock-on tracking mode in accordance with an aspect of the present invention.

Referring to FIG. 8, at step S100, the tracking and data acquisition aspects of ultrasound imaging system 10 are initialized. In particular, processor circuit 24 executes program instructions to determine the type of tracking elements that are associated with each of ultrasound probe 16 and interventional medical device 18, the communications rate between processor circuit 24 and each of ultrasound probe 16 and interventional medical device 18, the rate of data acquisition updating, and probe parameters. Such probe parameters may include, scan extent start point and end point, and the desired velocity of the movement of active ultrasound transducer array 66, with respect to the origin point 71 (see FIG. 5A), defining the 0, 0, 0 location in the X, Y, and Z axes. Also, the location of tracking elements of ultrasound probe 16 and interventional medical device 18 may be calibrated with respect to the 3D detection volume 38 defined by EM field generator 12 (see FIG. 1).

At step S102, "WHILE" defines the entry into a continuous loop to virtually converge the position of the ultrasound imaging plane of active ultrasound transducer array 66 of ultrasound probe 16 with the position of tracking element 44, and in turn distal tip 40, of interventional medical device 18. Processor circuit 24 remains in this continuous loop until the program execution is stopped.

At step S104, the current position of tracking element 44 of interventional medical device 18 is determined in relation to the 3D detection volume 38 defined by EM field generator 12. In particular, tracking element 44 of interventional medical device 18, generates tip location data as physical coordinates based on the EM locator field 36 generated by EM field generator 12, and provides the tip location data associated with the physical coordinates to processor circuit 24.

At step S106, in parallel to step S104, the current position of tracking element 64 of ultrasound (US) probe 16 is determined in relation to the 3D detection volume 38 defined by EM field generator 12. In particular, tracking element 64 of ultrasound probe 16 generates probe location data as physical coordinates based on the EM locator field 36 generated by EM field generator 12, and provides the probe location data associated with the physical coordinates to processor circuit 24.

At step S108, an ultrasound plane position (B-scan position) is determined based on the probe location data. In particular, processor circuit 24 executes program instructions to define a unit vector, i.e., the Z-axis at origin point 71 (0,0,0) of FIG. 5A, that is perpendicular to (e.g., points downwardly from) the surface of head portion 54 of ultrasound probe 16, wherein the unit vector initially lies on a current ultrasound image plane. Processor circuit 24 executes program instructions to virtually rotate the vector to be normal to the current ultrasound image plane. Processor circuit 24 then executes program instructions to rotate the normal vector about the Z-axis using the probe location data acquired at step S106, which corresponds to the orientation angle of ultrasound probe 16. Processor circuit 24 then executes program instructions to determine the position of the current ultrasound image plane, with respect to the origin, using the following equation:

$$\text{ultrasound plane position} = (Ax + By + Cz + D), \quad \text{Equation 1}$$

where A, B, C are coefficients of the x, y, z position coordinates (of the probe location data) defining the plane of ultrasound probe 16, and D is the length of the distance vector from the origin point 71 to the Ax+By+Cz plane.

At step S110, processor circuit 24 executes program instructions to calculate an offset distance between the position of interventional medical device 18, as defined by the tip location data, and the ultrasound plane position (determined at step S108) of ultrasound probe 16, by using the equation:

$$\text{OFFSET} = (Ax1 + By1 + Cz1 + D)/\text{sqrt}(A^2 + B^2 + C^2), \quad \text{Equation 2}$$

where: A, B, C, and D are coefficients of the ultrasound plane position (see step S108), and x1, y1, z1 are the position coordinates (of the tip location data) of interventional medical device 18.

The Equation 2 offset calculation gives the minimum, or perpendicular, distance from tracking element 44 of interventional medical device 18 to the ultrasound plane position, which is the distance (and direction) that ultrasound transducer mechanism 62 needs to move active ultrasound transducer array 66 so that there is a convergence (intersection) of the ultrasound position plane with the tracking element 44, and in turn distal tip 40, of interventional medical device 18. Thus, in essence, the calculation determines the offset used to achieve a convergence of the tip location data with the ultrasound plane position associated with the probe location data.

At step S112, ultrasound transducer mechanism 62 is driven to position active ultrasound transducer array 66 at the determined point of convergence as defined by the OFFSET calculated at step S110. In particular, processor circuit 24 executes program instructions to process the OFFSET to generate the positioning signal corresponding to the point of convergence, and the positioning signal is communicatively coupled to ultrasound transducer mechanism 62 to dynamically position active ultrasound transducer array 66 at a desired imaging location of the plurality of discrete imaging locations, so that the two-dimensional ultrasound slice data captured by active ultrasound transducer array 66 includes an image of at least the distal tip 40 of interventional medical device 18, so long as distal tip 40 of the interventional medical device 18 remains in the three-dimensional imaging volume 68 under the surface of the head portion of ultrasound probe 16.

In the embodiment of FIGS. 6A and 6B, the positioning signal will culminate in stepper motor control signal that are supplied to stepper motor 74. In the embodiment of FIGS. 7A and 7B, the positioning signal will culminate in a row selection signal supplied to two-dimensional ultrasound transducer array 84. As used herein, the terms "under" or "underlying" with respect to ultrasound probe 16, means within the possible imaging view extent of ultrasound probe 16.

Thereafter, the process returns to step S102, "WHILE", to continue in the continuous loop in maintaining a convergence of the position of the active ultrasound transducer array 66 of ultrasound probe 16 with tracking element 44, and in turn distal tip 40, of interventional medical device 18.

Figure 9:
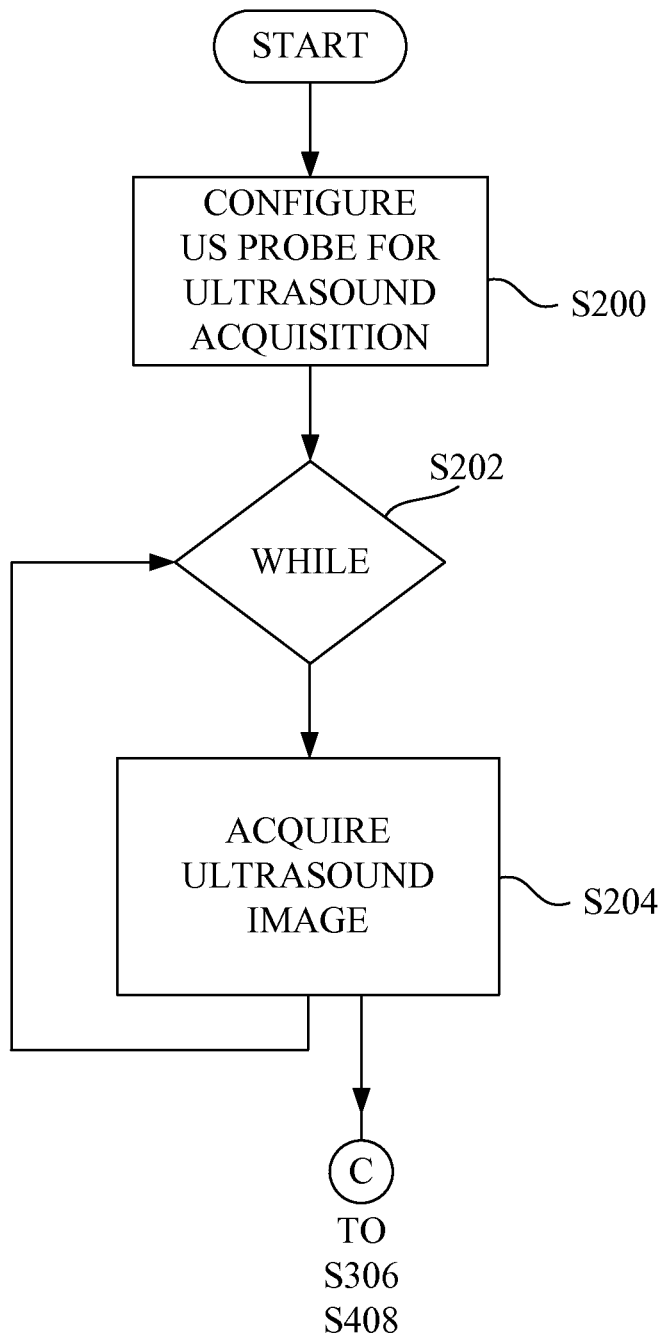
FIG. 9 is a flowchart depicting ultrasound data acquisition in accordance with an aspect of the present invention.

Referring to FIG. 9, there is shown a flowchart describing the acquisition of ultrasound data concurrently with, i.e., during, the "lock-on" function described above with respect to FIG. 8.

At step S200, ultrasound probe 16 is configured for acquisition of ultrasound data. For example, parameters such as the desired resolution, and emission strength of active ultrasound transducer array 66 to achieve a desired depth of penetration, may be set. For two-dimensional image scanning, ultrasound imaging system 10 is configured to collect a series of two-dimensional ultrasound imaging slices (ultrasound B-scan) data. For volume scan imaging, ultrasound imaging system 10 is configured to collect a series of ultrasound B-scan data to form three-dimensional ultrasound volumetric data representing the three-dimensional imaging volume 68, from which C-scan data, or other plane oriented data, may be derived.

At step S202, "WHILE" defines the entry into a continuous loop for acquisition of ultrasound data with active ultrasound transducer array 66 of ultrasound probe 16.

At step S204, ultrasound image data is acquired. More particularly, with reference to FIGS. 2 and 5A, processor circuit 24 is configured to execute program instructions, or alternatively includes circuitry, to process two-dimensional ultrasound slice data generated by the active ultrasound transducer array 66 of ultrasound transducer mechanism 62 of ultrasound probe 16, and to generate the ultrasound image for display at display screen 28 of graphical user interface 22. Also, processor circuit 24 may execute program instructions to automatically store the two-dimensional ultrasound slice data in non-transitory electronic memory 24-2, and thus accumulate multiple image data sets of the location of interest. Alternatively, graphical user interface 22 may provide a user command to processor circuit 24 to store the two-dimensional ultrasound slice data in non-transitory electronic memory 24-2 on demand at the command from a user.

For two-dimensional image scanning, a series of two-dimensional ultrasound imaging slices (ultrasound B-scan) data is collected and stored in non-transitory electronic memory 24-2. For volume scan imaging, active ultrasound transducer array 66 is scanned along the Y-axis across all, or a selected portion, of the three-dimensional imaging volume 68 to take a detailed volumetric scan of the underlying area beneath head portion 54 of ultrasound probe 16, such that a series of ultrasound B-scan data representing the three-dimensional imaging volume is collected and stored in non-transitory electronic memory 24-2.

Thereafter, the process returns to step S202, "WHILE", to continue in the acquisition and updating of the ultrasound data.

While relative movement of ultrasound probe 16 and the distal tip 40 of interventional medical device 18 will result in a movement of the location of distal tip 40 of interventional medical device 18 in the three-dimensional imaging volume 68, so long as tracking element 44 and thus distal tip 40 of interventional medical device 18 remains in the three-dimensional imaging volume 68 of ultrasound probe 16, ultrasound imaging system 10 is able to dynamically position active ultrasound transducer array 66 to converge at a desired imaging location of the plurality of discrete imaging locations in the three-dimensional imaging volume 68 so that the two-dimensional ultrasound slice data includes an image of at least the distal tip 40 of interventional medical device 18 in generating the ultrasound image displayed on display screen 28.

However, referring again to FIG. 5A, in the event that tracking element 44 of interventional medical device 18 is outside the three-dimensional imaging volume 68, a motion indicator 88 located on at least one of the ultrasound probe 16 and the display screen 28 of graphical user interface 22 (see also FIG. 2) is provided to guide the user to an acceptable placement of ultrasound probe 16 relative to the tracked interventional medical device 18. Motion indicator 88 is operably coupled to processor 24, and may be in the form of directional arrows that may be selectively illuminated by processor circuit 24 so as to guide the user to an acceptable placement of ultrasound probe 16 relative to the tracked interventional medical device 18.

In particular, based on the tip location data provided by tracking element 44 of interventional medical device 18 and the probe location data tracking element 64 of ultrasound probe 16 processed by processor circuit 24, processor circuit 24 executes program logic to determine whether tracking element 44 of interventional medical device 18 is outside the three-dimensional imaging volume 68, and thus is outside the imageable range of ultrasound probe 16.

For example, when ultrasound probe 16 having tracking element 64 and interventional medical device 18 having tracking element 44 are placed within detection volume 38 of the EM field generator 12, the location of both tracking element 44 and tracking element 64, and the relative distance between tracking element 44 and tracking element 64, are calculated by processor circuit 24. Using this location and distance information, processor circuit 24 executes program instructions to determine whether the distal tip 40 of the interventional medical device 18 is presently located outside the three-dimensional imaging volume 68. If so, processor circuit 24 of ultrasound imaging system 10 further executes program instructions to generate a visual prompt at motion indicator 88 to prompt the user to move head portion 54 of ultrasound probe 16 in a particular direction to a general location such that tracking element 44, and thus distal tip 40, of interventional medical device 18 resides in the three-dimensional imaging volume 68 under ultrasound probe 16, thereby permitting the active ultrasound transducer array 66 of ultrasound probe 16 to automatically capture ultrasound image data containing the tracking element 44 and distal tip 40 of interventional medical device 18 for display on display screen 28.

Thus, in practicing the "lock-on" functionality mode of action of the present invention, if the tracking element 44, and thus distal tip 40, of the interventional medical device 18 is outside the three-dimensional imaging volume 68 of ultrasound probe 16, manual probe positioning prompts will be generated, in the form of motion indicator 88, which is present on ultrasound probe 16 and/or on graphical user interface 22 to prompt the user to move ultrasound probe 16 to the general location that contains the interventional medical device 18 having tracking element 44, such that tracking element 44 and distal tip 40 of interventional medical device 18 lies within the three-dimensional imaging volume 68 of ultrasound probe 16.

Once the user has placed ultrasound probe 16 over the general area to be visualized, location information from ultrasound probe 16 and interventional medical device 18 is further used to move the position of the active ultrasound transducer array 66 of ultrasound probe 16, which allows ultrasound imaging system 10 to converge on a two-dimensional ultrasound image slice that includes the underlying interventional medical device 18, even if ultrasound probe 16 is not placed directly over tracking element 44/distal tip 40 of interventional medical device 18.

The position of the active ultrasound transducer array 66 of ultrasound probe 16 is dynamically adjusted in near real time, limited by data acquisition and processing speed, which allows ultrasound imaging system 10 to adapt to small changes in position of ultrasound probe 16, the position of the tracking element 44 of interventional medical device 18, and/or the patient position, such that an ultrasound image of the underlying interventional medical device 18 is maintained within view of ultrasound probe 16.

If the interventional medical device 18 to be imaged moves outside of the possible three-dimensional imaging volume 68 beneath ultrasound probe 16, positioning prompts in the form of motion indicator 88 are again generated and used to prompt the user to move ultrasound probe 16 in a direction that allows ultrasound imaging system 10 to again converge on, and display, an ultrasound image of the underlying interventional medical device 18.

Ultrasound imaging system 10 also may be operated in a three-dimensional (3D) high resolution scan imaging mode, with reference to step S204 of FIG. 9.

In general, with further reference to FIG. 5A, in the three-dimensional (3D) high resolution imaging mode the ultrasound probe 16 is held in a fixed position over an area of interest, and the active ultrasound transducer array 66 is scanned along the Y-axis across all, or a selected portion, of the three-dimensional imaging volume 68 to take a detailed volumetric scan of the underlying area beneath head portion 54 of ultrasound probe 16. Ultrasound probe 16 may be held in the fixed position by the hand of the user. Metadata containing the position location from each two-dimensional slice obtained in the high resolution mode is further used to identify images taken from the same point in space, and subsequently used for image integration processing.

More particularly, in the 3D high resolution imaging mode, processor circuit 24 of ultrasound console 14 is configured to execute program instructions to generate a scanning signal that is supplied to ultrasound transducer mechanism 62 to scan active ultrasound transducer array 66 over at least a portion of the three-dimensional imaging volume 68. The active ultrasound transducer array 66 is repeatedly actuated during the scan to generate a plurality, i.e., a series, of sequential two-dimensional ultrasound slices, which are stored in memory 24-2, and combined to form the 3D ultrasound volumetric data from which a three-dimensional (3D) high resolution ultrasound image is formed and displayed on display screen 28 of graphical user interface 22 (see also FIG. 2).

The quality of the high resolution 3D images may be improved by generating a composite ultrasound image of the location of interest. Because the location of the ultrasound probe 16 is known by processor circuit 24, multiple sets of 2D or 3D, ultrasound images of a particular location in the three-dimensional imaging volume 68 underlying, e.g., perpendicular to, the surface of the head portion 54 of ultrasound probe 16 may be taken, and stored in non-transitory electronic memory 24-2, from which a compound composite ultrasound image may be generated from the multiple sets of 2D, or 3D, ultrasound images by summing together the multiple sets of ultrasound images of the same location.

In particular, processor circuit 24 is configured to execute program instructions to operate the active ultrasound transducer array 66 to generate multiple sets of ultrasound image data that includes metadata corresponding to a particular location, i.e., metadata describing the location of the scan within the three-dimensional volume 68, and save the multiple sets in non-transitory electronic memory 24-2. Processor circuit 24 is further configured to execute program instructions to sum the multiple sets of ultrasound image data to generate composite (compound) ultrasound image data, which is then stored in non-transitory memory 24-2 and/or is displayed on display screen 28 of graphical user interface 22.

Figure 10:
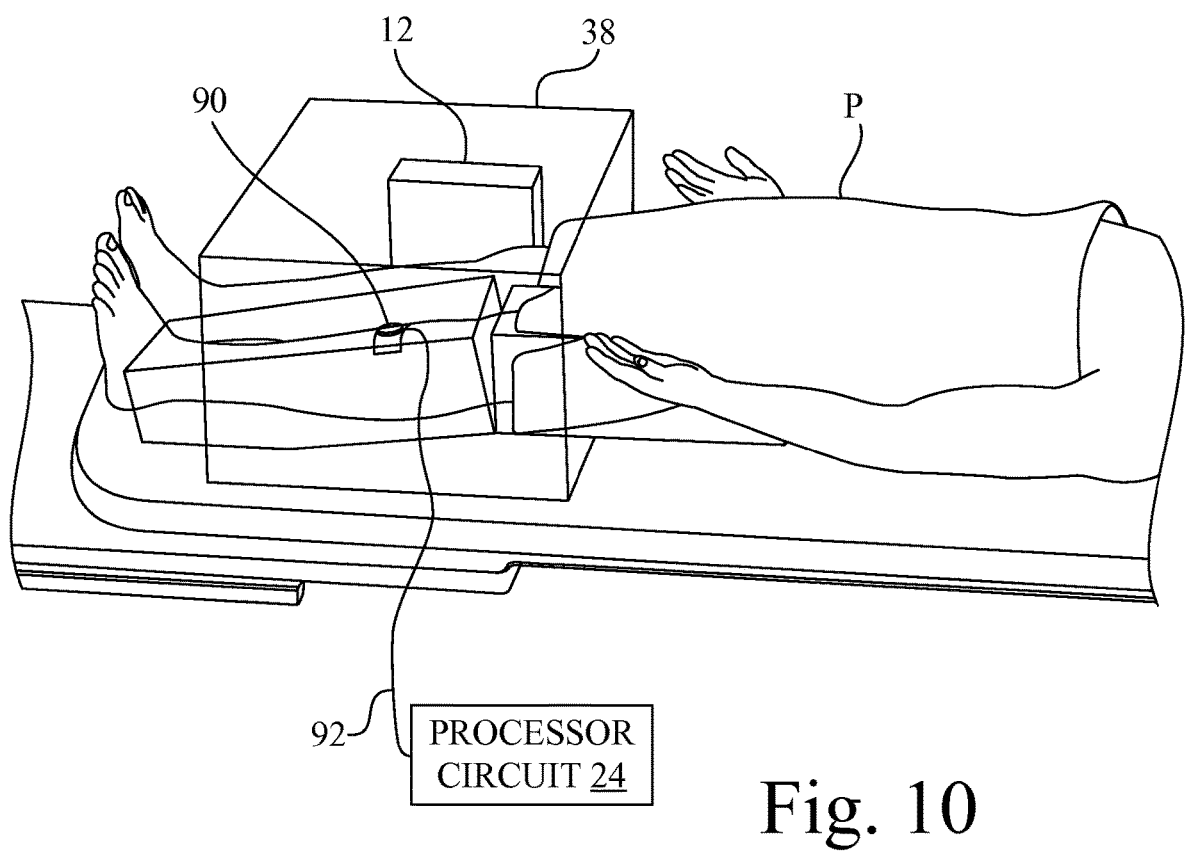
FIG. 10 shows a general side view of a patient having a position tracking element affixed to the skin.

Referring also to FIG. 10, the quality of the high resolution 3D images also may be improved by tracking the position of the patient P in relation to the position of ultrasound probe 16 to reduce motion artifacts in the 3D images. A third EM tracking element 90 (i.e., a wire electrical tracking coil), is affixed to the patient, such as by an adhesive. Tracking element 90 is communicatively coupled to processor circuit 24 of ultrasound console 14 by a communication link 92, such as a wired or wireless connection. Tracking element 90, when energized by electromagnetic (EM) field generator 12, generates three-axis patient location data, which is supplied via communications link 92 to processor circuit 24. Processor circuit 24 processes the three-axis patient location data to further adjust the position of the active ultrasound transducer array 66 of ultrasound probe 16 in response to any motion of the patient. In other words, tracking element 90 allows for the position of the patient to be known, which in turn allows ultrasound imaging system 10 to adjust the position of the active ultrasound transducer array 66 of ultrasound probe 16 to any motion created by the patient.

Ultrasound imaging system 10 also may be operated to render and display one or more synthetic (user chosen) scan planes.

Figure 11:
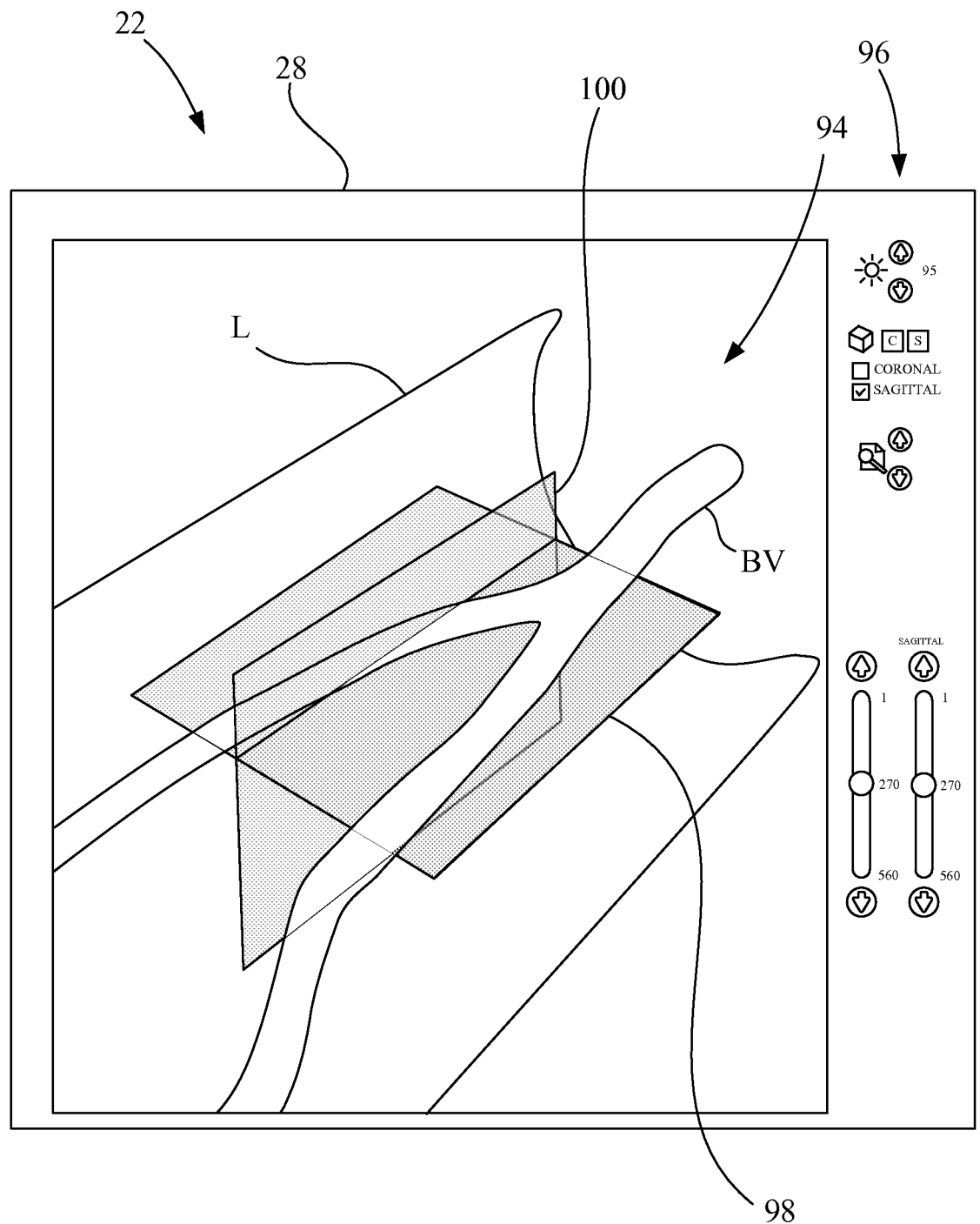
FIG. 11 shows a screen of the graphical user interface of FIG. 1, configured to display one or more synthetic (user chosen) scan planes, such as a coronal scan plane and an axial (sagittal) scan plane.

Referring also to FIG. 11, there is shown the graphical user interface 22 having a three-dimensional ultrasound image 94 and user controls 96 displayed on display screen 28. As described above, a plurality, i.e., a series, of sequential two-dimensional ultrasound slices may be generated and combined to generate 3D ultrasound volumetric data defining a three-dimensional imaging volume. Using the 3D ultrasound volumetric data acquired from ultrasound probe 16, the user may select for rendering and display one or more synthetic (user chosen) scan planes, such as a coronal scan plane 98 and an axial (sagittal) scan plane 100.

In particular, the user may define, using user controls 96, a desired synthetic plane orientation with respect to the 3D ultrasound volumetric data associated with three-dimensional ultrasound image 94. From the plane orientation inputs provided at user controls 96, processor circuit 24 of ultrasound imaging system 10 executes program instructions to identify within the 3D ultrasound volumetric data of three-dimensional ultrasound image 94 the image data associated with the desired synthetic plane orientation. The desired synthetic plane may pass through multiple two-dimensional image data slices in the 3D ultrasound volumetric data. Once the image data associated with the desired synthetic plane orientation within the 3D ultrasound volumetric data is identified, the desired one or more synthetic (user chosen) scan planes may be rendered and displayed on display screen 28 of graphical user interface 22 within the generated three-dimensional ultrasound image 94 as shown in FIG. 11, or as standalone two-dimensional images. These additional views may allow for further inspection of the underlying anatomy, beyond what is normally obtained via fluoroscopy, which in turn may result in improved clinical outcomes.

Various views, such as those associated with the sagittal plane, the transverse plane, and the coronal plane, may be visualized, and a slice from one or more, or all, of the planes, as defined by the location of the tracked device(s), e.g., tracking element 44 of interventional medical device 18 and/or tracking element 64 of ultrasound probe 16, can be displayed, individually or as a group. It is also envisioned that scan planes that do not exist at 90 degrees from each other could also be defined and selected by the user. Additionally, the user defined scan planes may not be planar, and may follow a curved path.

Another aspect of the present invention provides for a focusing of the three-dimensional imaging volume around a determined region of interest, i.e., the region around the location of tracking element 44 of interventional medical device 18, by reducing the scan extent along the Y-axis (see FIG. 5A), thus reducing the amount of three-dimensional ultrasound volumetric data required to adequately view the region surrounding interventional medical device 18. In other words, following an initial 3D ultrasound volumetric data scan, on a subsequent 3D ultrasound volumetric data scan centered on the determined region of interest, the scan extent of active ultrasound transducer array 66 along the Y-axis is reduced, i.e., focused, to that of most interest, thus reducing scanning time and the amount of data required to adequately represent the three-dimensional volume of interest.

In particular, processor circuit 24 executes program instructions to determine a region of interest in the three-dimensional ultrasound volumetric data defining the three-dimensional imaging volume 68. Processor circuit 24 also executes program instructions to reduce the scan range of the active ultrasound transducer array 66 of the ultrasound transducer mechanism 62 along the Y-axis for acquisition of subsequent three-dimensional ultrasound volumetric data at the region of interest from that of the scan range of the previous scan, so as to reduce the amount of acquired three-dimensional ultrasound volumetric data from that of the prior scan.

Figure 12:
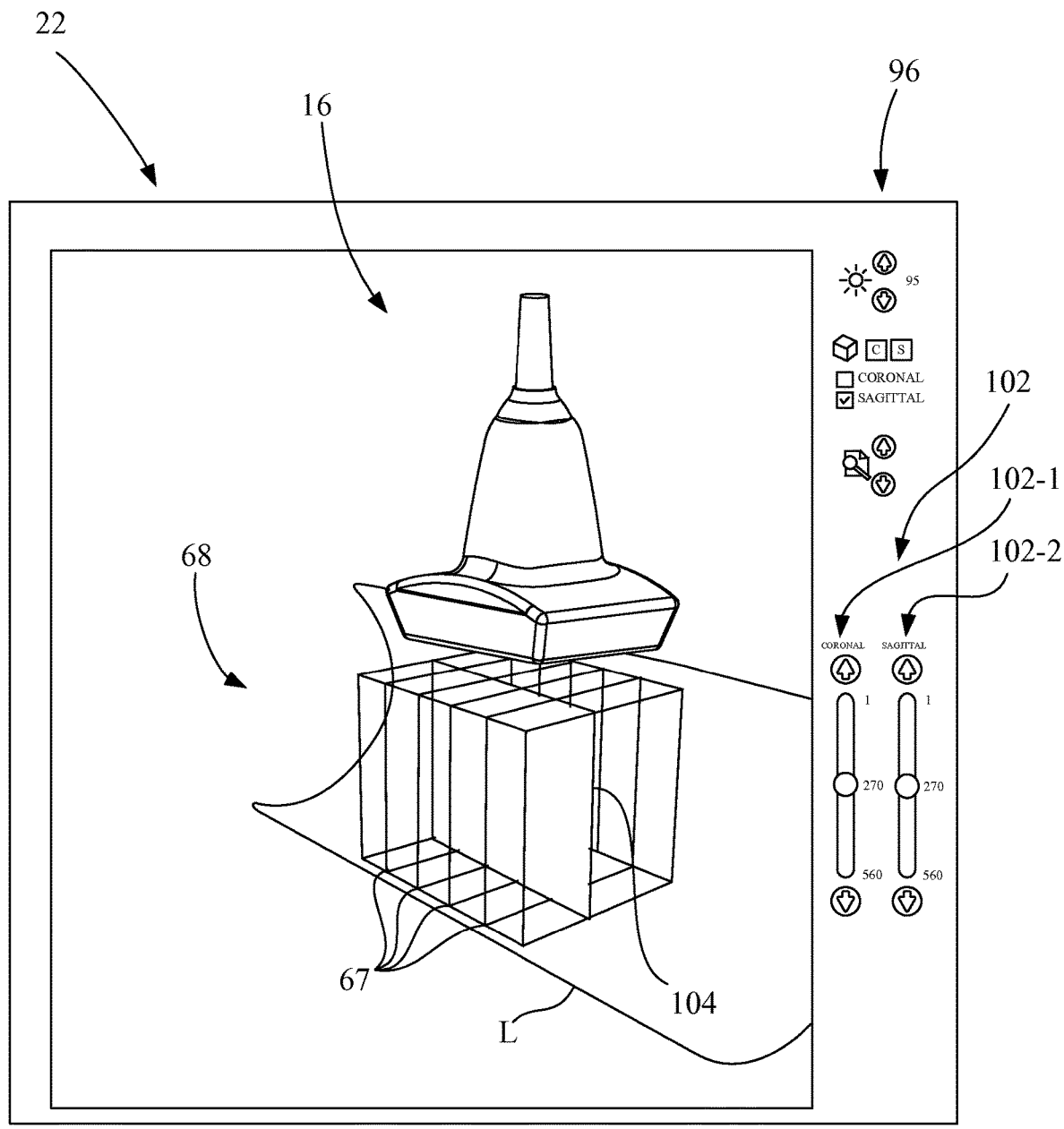
FIG. 12 is a pictorial representation of the graphical user interface of FIG. 1 depicting a sagittal plane slice extending through a series of two-dimensional ultrasound image slices in a three-dimensional imaging volume at sagittal slice location 270.
Figure 13:
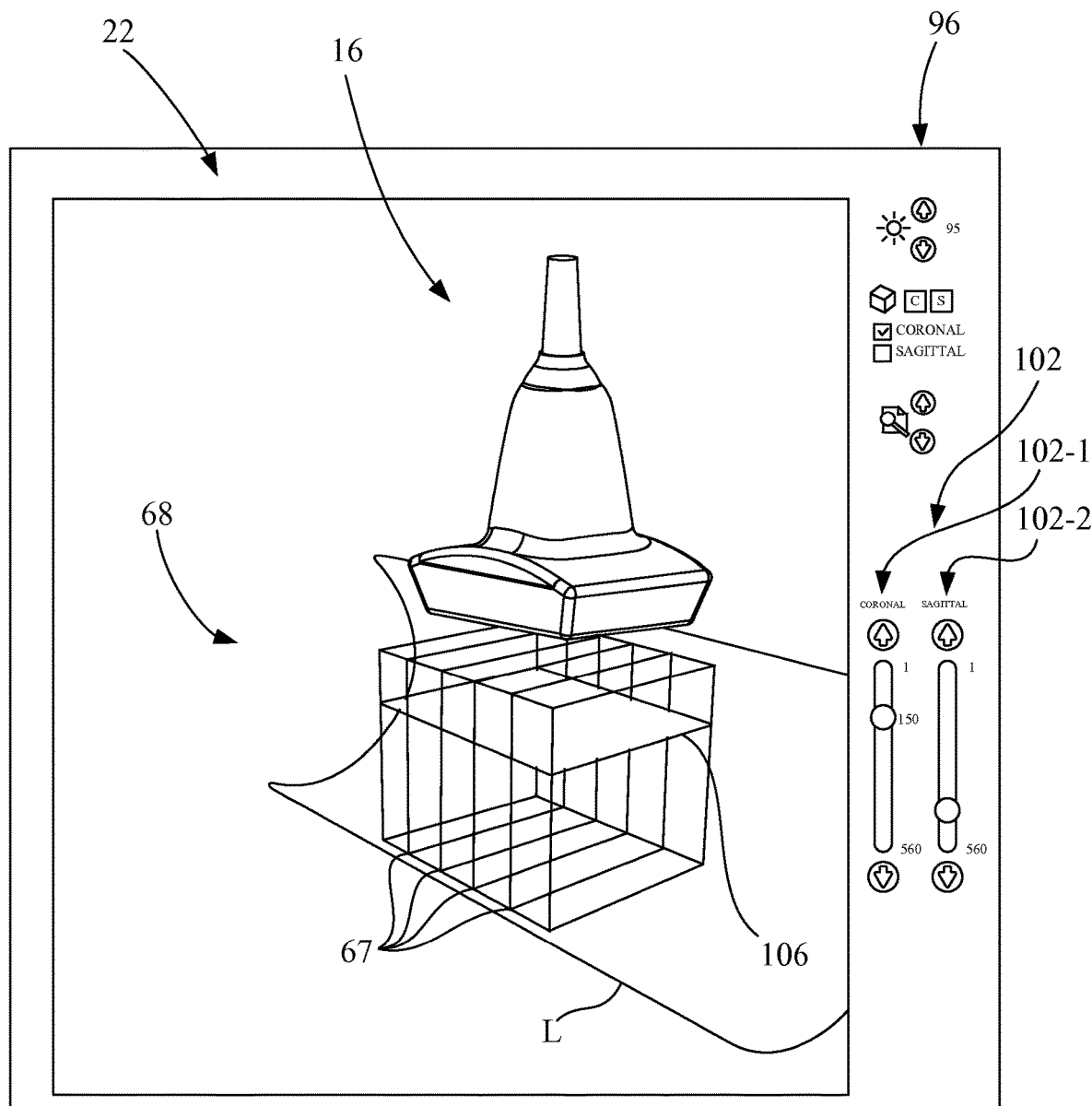
FIG. 13 is a pictorial representation of the graphical user interface of FIG. 1 depicting a coronal plane slice extending through a series of two-dimensional ultrasound image slices in a three-dimensional imaging volume at coronal slice location 150.

Referring to FIGS. 12 and 13, as another aspect of the present invention, user controls 96 of graphical user interface 22 may include one or more slice selection sliders 102, such as a coronal slider 102-1 and a sagittal slider 102-2, to provide a sequential variation from an automatically, or manually, selected two-dimensional ultrasound image slice being displayed.

Referring also to FIG. 5A, a plurality, i.e., a series, of sequential two-dimensional ultrasound B-scan imaging slices 67 may be generated and combined to generate 3D ultrasound volumetric data defining a three-dimensional imaging volume 68. As such, based on tracking of the location of tracking element 44 of interventional medical device 18 and tracking element 64 of ultrasound probe 16, a desired two-dimensional ultrasound image slice on a desired imaging plane may be generated from the 3D ultrasound volumetric data that includes a particular region of interest, such as distal tip 40 of interventional medical device 18. The desired two-dimensional ultrasound image slice may be in an imaging plane different from that of the native B-scan imaging plane of the sequential two-dimensional ultrasound imaging slices 67 that when combined form the 3D ultrasound volumetric data defining the three-dimensional imaging volume 68.

Thus, slice selection sliders 102 permit the user to select a slice in each of one or more imaging planes for display, if desired, wherein the selected two-dimensional ultrasound image slice may intersect, or lie on either side of, the two-dimensional ultrasound image slice that was automatically, or manually, selected. The slice selection sliders 102 are configured to provide a sequential parallel variation from the initially selected two-dimensional ultrasound image slice to manually select a second two-dimensional ultrasound image slice parallel to the initially selected two-dimensional ultrasound image, wherein the second two-dimensional ultrasound image slice lies on either side of the initially selected two-dimensional ultrasound image slice.

For example, FIG. 12 is a pictorial representation at graphical user interface 22 depicting a selection of a sagittal plane slice 104 extending through a series of two-dimensional ultrasound image slices 67 in the three-dimensional imaging volume 68 at sagittal slice location 270. By manipulation of sagittal slider 102-2 using one of the up-down arrows, sagittal slice location 271, or others 1-269 or 272-560, parallel to the sagittal slice location 270 may be selected for display. Likewise, FIG. 13 is a pictorial representation depicting a selection of a coronal plane slice 106 extending through a series of two-dimensional ultrasound image slices 67 in a three-dimensional imaging volume 68 at coronal slice location 150. By manipulation of coronal slider 102-1 using one of the up-down arrows, coronal slice location 151, or others 1-149 or 152-560, may be selected for display.

Figure 14:
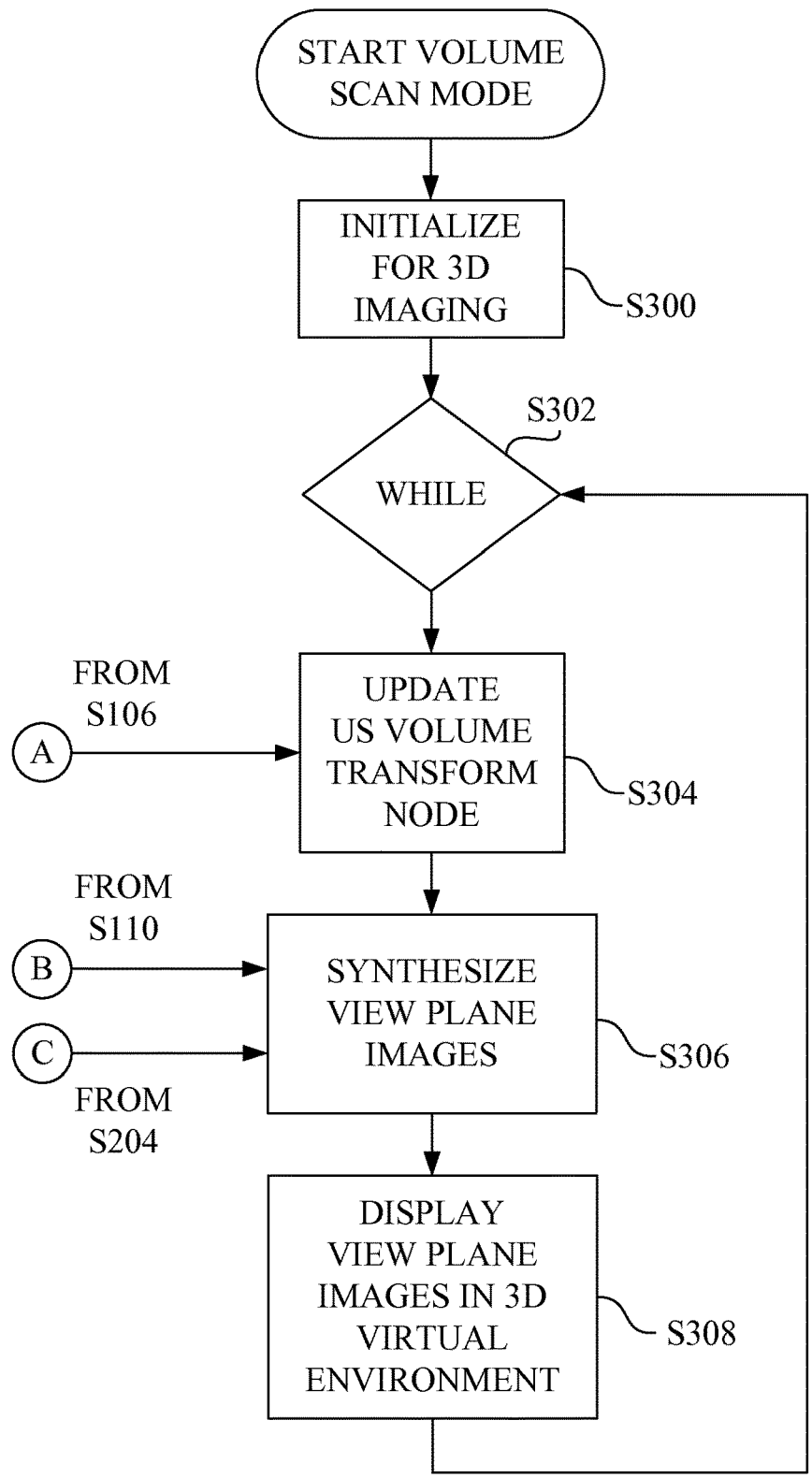
FIG. 14 is a flowchart describing the generation of a set of ultrasound images derived or synthesized from the three-dimensional volume data set, and shown in the correct location in the 3D virtual environment, in accordance with an aspect of the present invention.

Referring to FIG. 14, there is shown a flowchart describing the generation of a 3D ultrasound image as a set of three orthogonal ultrasound images.

At step S300, ultrasound imaging system 10 is initialized for rendering a 3D ultrasound image as a set of three orthogonal images, such as setting up processor circuit 24 and graphical user interface 22 for construction of 3D models.

At step S302, "WHILE" defines the entry into a continuous loop for generation and updating of the displayed 3D ultrasound image.

At step S304, an ultrasound (US) volume transform node is updated based on the position of ultrasound probe 16, as determined at step S106 of FIG. 8. In particular, processor circuit 24 executes program instructions to move the 3D model of the three-dimensional imaging volume 68 to match the current position of ultrasound probe 16.

At step S306, using the calculated OFFSET from step S110 of FIG. 8, and the 3D image data acquisition as described at step S204 of FIG. 9, processor circuit 24 executes program instructions to choose a two-dimensional ultrasound imaging slice 67 (B-scan) from a C-scan data slice that includes the tracking element 44, and in turn the distal tip 40, of interventional medical device 18.

At step S308, processor circuit 24 executes program instructions to generate 3D display data representative of three orthogonal images in a virtual 3D environment associated with the three-dimensional imaging volume 68 matched to the current position of ultrasound probe 16. Processor circuit 24 sends the 3D display data to user interface 22 for display on display screen 28 as three orthogonal images that include the tracking element 44, and in turn the distal tip 40, of interventional medical device 18.

Thereafter, the process returns to step S302, "WHILE", to continue updating the displayed 3D ultrasound image.

Referring now to FIGS. 15A, 15B, 15C and 16, there is described below a patient oriented imaging window mode. In the past, that which was rendered as "up" on the ultrasound display screen followed the orientation of the ultrasound probe. However, in this aspect of the present invention, the orientation of the displayed ultrasound image is true to the orientation of the patient, regardless of the actual orientation of the ultrasound probe.

Figure 15A:
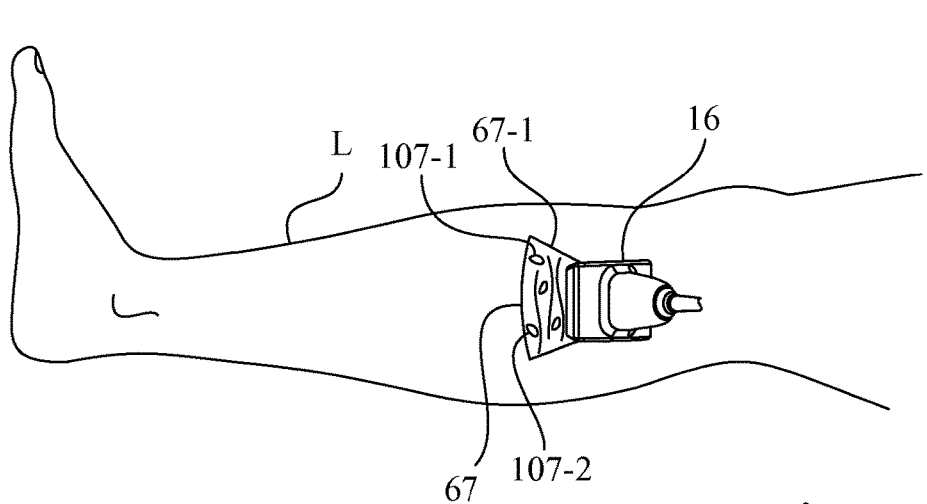
FIG. 15A is a diagrammatic illustration of the ultrasound probe of FIG. 1 taking a two-dimensional ultrasound imaging slice of a portion of a leg of a patient.

FIG. 15A shows a diagrammatic illustration of ultrasound probe 16 taking a two-dimensional ultrasound imaging slice 67 of a portion of a leg L of a patient. For purposes of comparison, note the location and orientation of the upper blood vessel 107-1, and the lower-left blood vessel 107-2, in relation to the orientation of the leg L of a patient P.

Figure 15B:
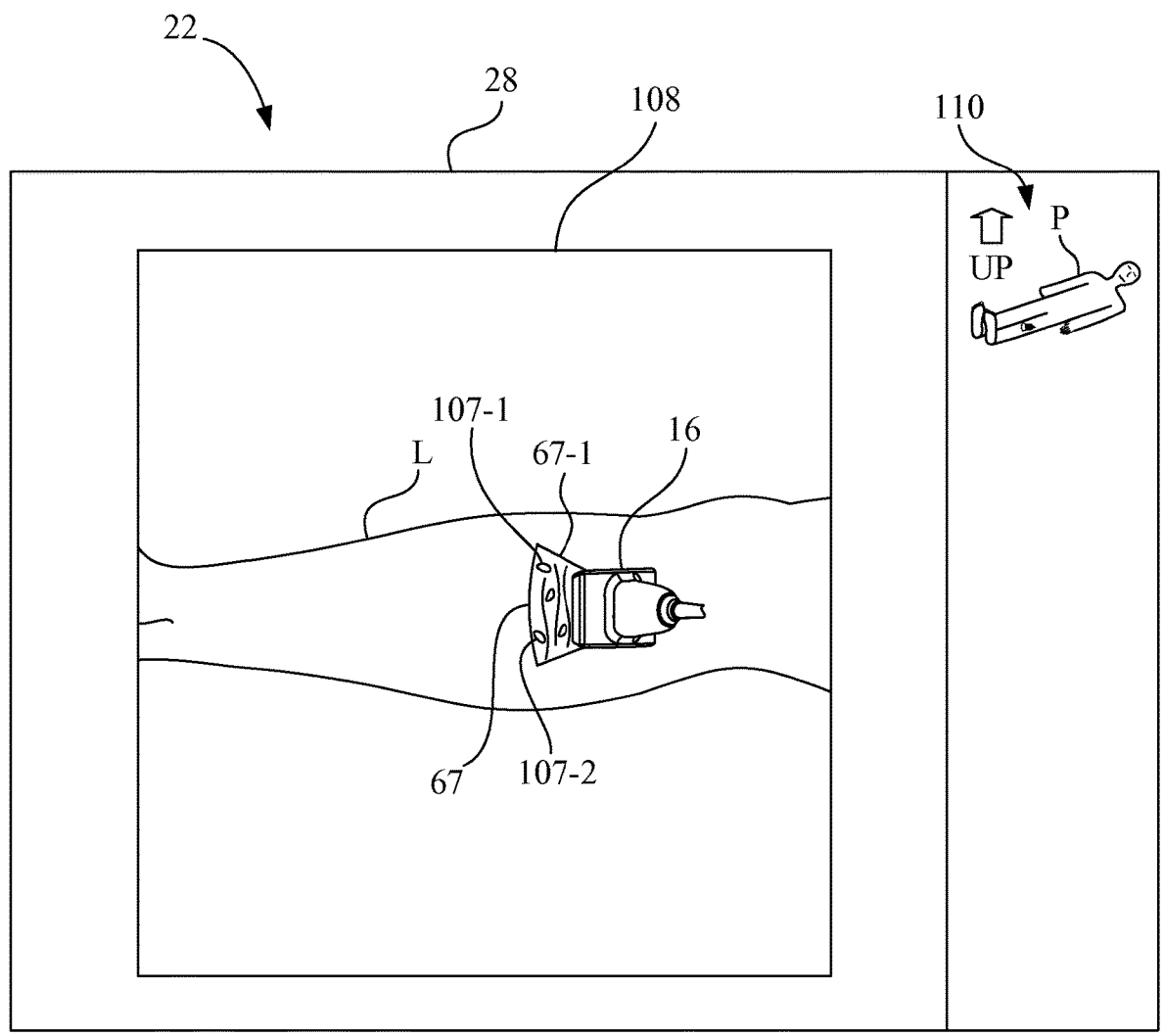
FIG. 15B is a diagrammatic illustration of the graphical user interface of FIG. 1 having a patient oriented imaging window depicting a patient oriented virtual environment, wherein the location and orientation of the acquired ultrasound image data is rendered on the display screen to correspond to the orientation of the patient, such that the orientation and location of where the image is being acquired relative to the patient can be indicated and communicated to the viewer via use of the virtual environment.

FIG. 15B is a diagrammatic illustration of graphical user interface 22 having a patient oriented imaging window 108 depicting a patient oriented virtual environment on display screen 28 of graphical user interface 22, wherein the location and orientation of the acquired ultrasound image data is rendered on the display screen 28 to correspond to the orientation of the patient P, wherein the orientation and location of where the ultrasound image is being acquired relative to a position of the patient P is indicated and communicated to the clinician via use of the virtual environment. In particular, FIG. 15B shows a diagrammatic illustration of graphical user interface 22 having patient oriented imaging window 108 including an image of leg L, rendered as an actual image of patient leg L or as a computer generated virtual rendering, and including a virtual rendering of ultrasound probe 16 and two-dimensional ultrasound imaging slice 67 that is generated by ultrasound probe 16. Also shown is a secondary imaging window 110 including a computer generated virtual rendering, i.e., a graphic, of the orientation of the body of patient P, as well as an UP arrow indicating the orientation of the UP relative to the patient.

Figure 15C:
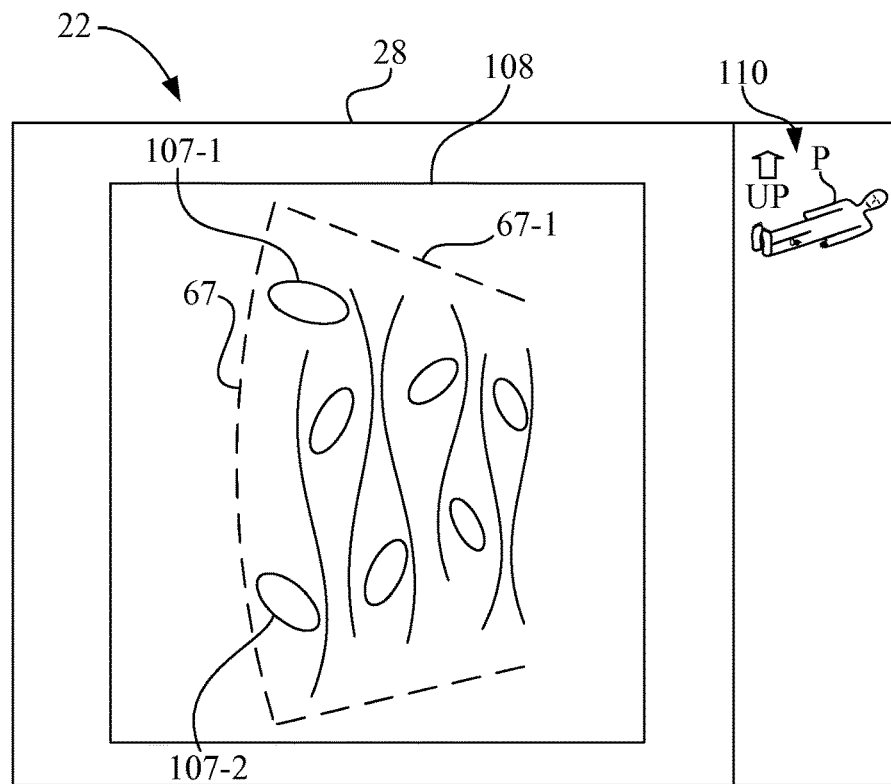
FIG. 15C is a full view of the ultrasound image shown in FIG. 15B, in which the orientation of the location and orientation of the acquired ultrasound image data is rendered on the display screen to correspond to the orientation of the patient.

Referring also to FIG. 15C, since the orientation of ultrasound probe 16 is known to ultrasound imaging system 10, as described above, the display of the ultrasound image on display screen 28 of graphical user interface 22 may be adjusted such that a vertical "top" 67-1 of the acquired ultrasound image data of two-dimensional ultrasound imaging slice 67, or the vertical top of the acquired volumetric data in 3D data acquisition, is always rendered as "UP" on display screen 28 relative to the position of the patient P, and regardless of the actual orientation of ultrasound probe 16 relative to the patient. In other words, even if the actual orientation of ultrasound probe 16 is changed relative to the position of the leg L from that depicted in FIG. 15B, such as the head of ultrasound probe 16 pointing downward, the orientation of the ultrasound image on display screen 28 of graphical user interface 22 remains as depicted in FIG. 15C. Thus, as viewed in display screen 28, features of the displayed image, such as the upper blood vessel 107-1, and the lower-left blood vessel 107-2, are always displayed in the correct orientation relative to the patient P.

Figure 15D:
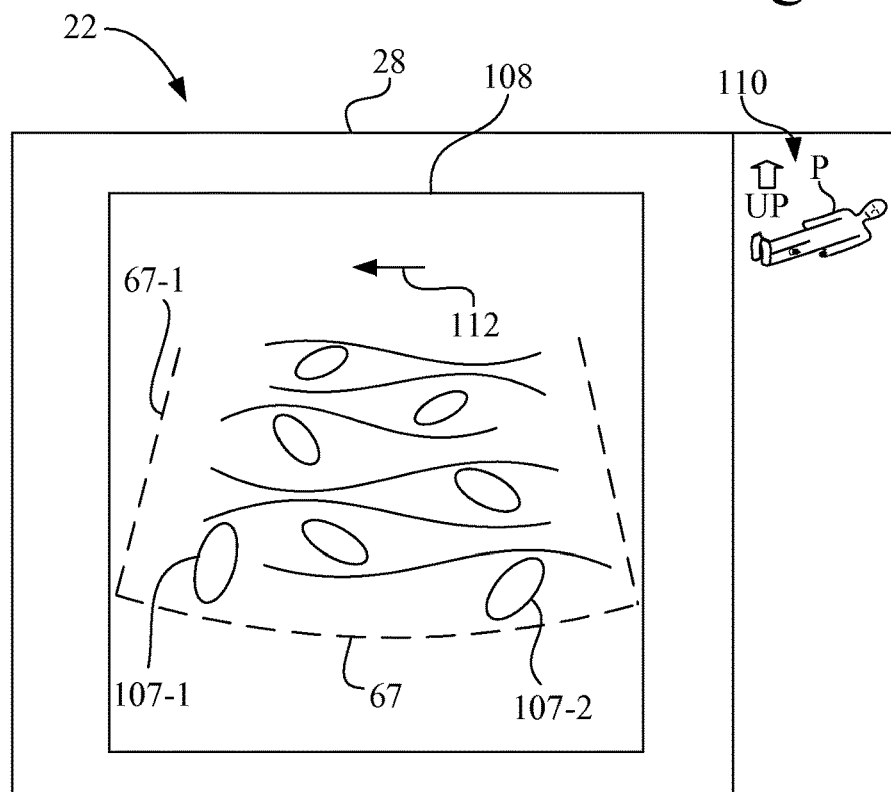
FIG. 15D is a comparative view of the ultrasound image shown in FIG. 15B when rendered in accordance with the prior art, wherein the orientation of the acquired ultrasound image data rendered on the display screen does not correspond to the orientation of the patient.

In comparison, FIG. 15D depicts the ultrasound image generated in FIG. 15A as it would be rendered in accordance with the prior art, wherein the orientation of the acquired ultrasound image data rendered on the display screen does not correspond to the orientation of the patient. This is because in the prior art, the image is rendered on the display screen wherein the ultrasound probe head is in a virtual position at the top of the display screen and the bottom on the display screen always corresponds to the distal extent of the generated ultrasound image. More particularly, with the ultrasound probe oriented as depicted in FIGS. 15A and 15B, the prior art rendered ultrasound image would position the upper blood vessel 107-1 and the lower-left blood vessel 107-2 on the display screen as shown in FIG. 15D (i.e., rotated 90 degrees from that depicted in FIG. 15C), and as such, the displayed image no longer corresponds to the orientation of the patient P. Rather, as shown in FIG. 15D, using arrow 112 to designate the true "up" orientation, the prior art ultrasound image is actually rendered to face toward the left on the display screen. Accordingly, in the prior art, the ultrasound technician was required to mentally associate the orientation of the displayed image with that of the actual orientation of the patient.

Advantageously, the patient oriented imaging window aspect of the present invention described above with respect to FIGS. 15A, 15B and 15C, generates a virtual environment that aids a clinician, including a person not experienced in ultrasound imaging, in successful image acquisition.

Figure 16:
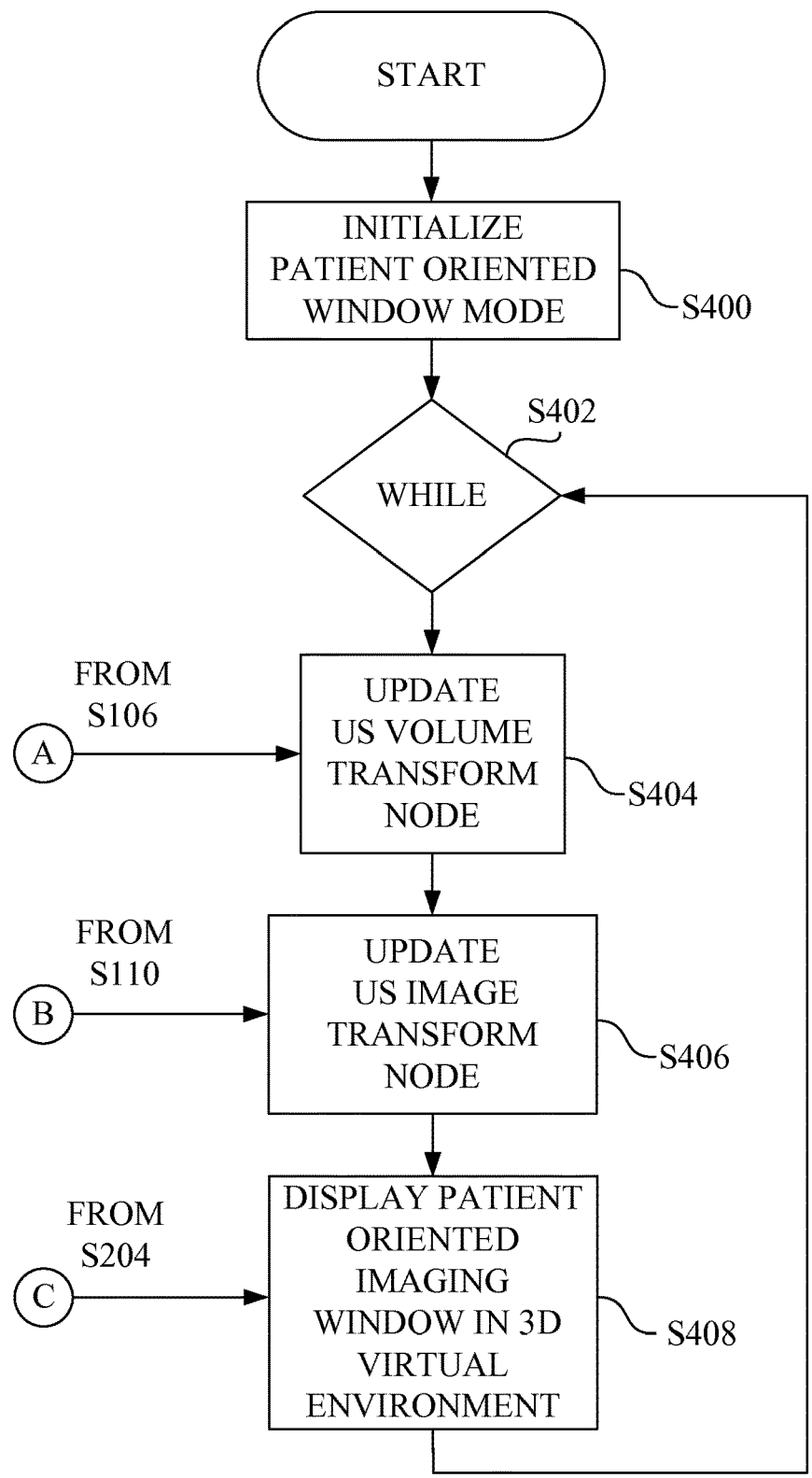
FIG. 16 is a flowchart of a patient oriented imaging window mode, or virtual environment imaging mode, associated with the depiction of the patient oriented imaging window of FIG. 15B shown in the correct location in the 3D virtual environment, in accordance with an aspect of the present invention.

More particularly, FIG. 16 is a flowchart of a patient oriented imaging window mode, i.e., a virtual environment imaging mode, associated with the generation of the patient oriented imaging window as depicted above with respect to FIGS. 15A, 15B and 15C.

At step S400, ultrasound imaging system 10 is initialized for rendering a 3D ultrasound image, such as setting up processor circuit 24 and graphical user interface 22 for construction of 3D models, initializing a camera video data transfer, and configuring appropriate patient lighting for video.

At step 402, "WHILE" defines the entry into a continuous loop for generation and updating of the displayed patient oriented imaging window 108 as depicted in FIGS. 15B and 15C.

At step S404, an ultrasound (US) volume transform node is updated based on the position of ultrasound probe 16, as determined at step S106 of FIG. 8. In particular, processor circuit 24 executes program instructions to move the 3D model of the three-dimensional imaging volume 68 (see FIG. 5A) to match the current position of ultrasound probe 16.

At step S406, an ultrasound (US) image transform node is updated based on the calculated OFFSET from step S110 of FIG. 8. In particular, processor circuit 24 executes program instructions to update the ultrasound image transform node by moving a 3D model of the three-dimensional ultrasound imaging data to match the current two-dimensional ultrasound imaging slice 67 (B-scan) acquired from ultrasound probe 16.

At step 408, based on 2D and/or 3D image data acquisition as described at step S204 of FIG. 9, processor circuit 24 executes program instructions to display the two-dimensional ultrasound imaging slice 67 (B-scan) in a 3-D environment in the patient oriented imaging window 108, such that the vertical "top" 67-1 of the acquired ultrasound image data of two-dimensional ultrasound imaging slice 67, or the vertical top of the acquired volumetric data in 3D data acquisition, is always rendered as "up" on display screen 28 relative to the position of the patient, and regardless of the actual orientation of ultrasound probe 16 relative to the patient.

Thereafter, the process returns to step 402, "WHILE", to continue in updating the patient oriented imaging window 108.

As an additional aspect, since the offset distance (z-axis) between the ultrasound probe 16 and the interventional medical device 18 can be calculated using Equations 1 and 2 (see steps S108 and S110, discussed above), this offset, or depth information, can further be used to dynamically control some of the ultrasound imaging settings in near real time, as identified below. This allows the system to optimize the image quality settings such that the best image of the interventional medical device 18 is displayed to the user at display screen 28. The ultrasound imaging settings that may be dynamically controlled because the z-axis offset from the ultrasound probe 16 can be calculated may include:

1) Ultrasound focus; such that the lateral resolution is optimized at the depth that contains the interventional medical device 18. Using the z-axis offset between the ultrasound probe 16 and the interventional medical device 18, the focus can be automatically adjusted to the depth that contains the interventional medical device 18.

2) Depth setting; because the z-axis offset from the ultrasound probe 16 can be calculated, the Depth setting can be dynamically controlled such that the depth of imaging is automatically adjusted to match the depth of the interventional medical device 18.

3) Zoom; because the z-axis offset from the ultrasound probe 16 can be calculated, the imaging window can be "zoomed" such that a larger view of the area of interest may be automatically displayed to the user.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An ultrasound imaging system, comprising:
    an electromagnetic (EM) field generator configured to generate an EM locator field;
    an interventional medical device defined by an elongate body having a distal tip and a distal end portion extending proximally from the distal tip, and having a first tracking element mounted in the distal end portion of the interventional medical device, the first tracking element being configured to generate tip location data based on the EM locator field;
    an ultrasound probe having a probe housing, an ultrasound transducer mechanism, and a second tracking element, the probe housing having a handle portion and a head portion, the ultrasound transducer mechanism and the second tracking element being mounted to the probe housing, the ultrasound transducer mechanism having an active ultrasound transducer array configured to generate two-dimensional ultrasound slice data at any of a plurality of discrete imaging locations within a three-dimensional imaging volume associated with the head portion, the active ultrasound transducer array configured to physically move relative to the probe housing, the second tracking element being configured to generate probe location data based on the EM locator field;
    a display screen; and
    a processor circuit communicatively coupled to the first tracking element, the second tracking element, the ultrasound transducer mechanism, and the display screen, the processor circuit configured to execute program instructions to process the two-dimensional ultrasound slice data to generate an ultrasound image within a virtual 3D environment for display at the display screen, and
    wherein the processor circuit is configured to execute program instructions to calculate an ultrasound plane position based on the probe location data, the processor circuit is configured to execute program instructions to calculate an offset distance between the tip location data of the interventional medical device and the ultrasound plane position, the processor circuit is configured to generate a positioning signal based on the offset distance to dynamically position the active ultrasound transducer array at a desired imaging location of the plurality of discrete imaging locations such that the two-dimensional ultrasound slice data includes at least the distal tip of the interventional medical device so long as a location of the distal tip of the interventional medical device remains in the three-dimensional imaging volume, the processor circuit is configured to execute program instructions to update the virtual 3D environment on the display screen to match the current position of the ultrasound probe, and the processor circuit is configured to execute program instructions to display the two-dimensional ultrasound slice data in the virtual 3D environment on the display screen such that the vertical top of the virtual 3D environment is rendered "up" on the display screen relative to a patient's orientation, regardless of an actual orientation of the ultrasound probe.

2. The ultrasound imaging system of claim 1, wherein relative movement of the ultrasound probe and the distal tip of the interventional medical device results in a movement of the distal tip of the interventional medical device with respect to the three-dimensional imaging volume, the system further comprising:
    a motion indicator located on at least one of the ultrasound probe and the display screen; and
    the processor circuit operably coupled to the motion indicator, wherein if the processor circuit determines that the distal tip of the interventional medical device is presently located outside the three-dimensional imaging volume, the processor circuit further executes program instructions to generate a visual prompt at the motion indicator to prompt the user to move the head portion of the ultrasound probe in a particular direction to a general location such that the distal tip of the interventional medical device resides in the three-dimensional imaging volume.

3. The ultrasound imaging system of claim 1, wherein the ultrasound transducer mechanism includes:
    a motion unit for performing linear movement and configured to effect rotational-to-linear translation conversion;
    a one-dimensional ultrasound transducer array as the active ultrasound transducer array, the one-dimensional ultrasound transducer array being connected to the motion unit for movement in unison with the motion unit; and
    a carriage,
    the motion unit including a stepper motor having a rotatable shaft, the stepper motor being operably connected to the processor circuit to rotate the rotatable shaft based on the positioning signal generated by the processor circuit, the rotatable shaft being drivably coupled to the carriage, wherein the carriage converts a rotation of the rotatable shaft of the stepper motor to a translation of the one-dimensional ultrasound transducer array to position the one-dimensional ultrasound transducer array at the desired location dictated by the positioning signal.

4. The ultrasound imaging system of claim 3, wherein the head portion having a planar surface, the planar surface having an origin point, the processor circuit is configured to execute program instructions to define a unit vector that begins at the origin point, the unit vector extends downwardly at a perpendicular angle to the planar surface, the processor circuit is configured to execute program instructions to calculate the ultrasound plane position based on the probe location data with respect to the origin point, the active ultrasound transducer array is configured to generate a current two-dimensional ultrasound slice data at the desired location, the processor circuit is configured to execute program instructions to virtually rotate the unit vector to be normal to the current two-dimensional ultrasound slice data.

5. The ultrasound imaging system of claim 4, wherein the processor circuit is configured to execute program instructions to update the virtual 3D environment on the display screen to match the current two-dimensional ultrasound slice data acquired from the ultrasound probe.

6. The ultrasound imaging system of claim 1, wherein the transducer mechanism includes a two-dimensional ultrasound transducer array having a plurality of columns and a plurality of rows of ultrasound transducer elements arranged in a matrix pattern, wherein one row of the plurality of rows of discrete ultrasound transducer elements is selected as the active ultrasound transducer array based on the positioning signal.

7. The ultrasound imaging system of claim 1, wherein the interventional medical device is one of a catheter, a lesion crossing catheter, a guide wire, a sheath, an angioplasty balloon, a stent delivery catheter, and a needle.

8. The ultrasound imaging system of claim 1, the ultrasound imaging system having a three-dimensional imaging mode, wherein with the ultrasound probe held in a fixed position over an area of interest, the processor circuit is configured to execute program instructions to generate a scanning signal with a scan range for a first scan that is supplied to the ultrasound transducer mechanism to scan the active ultrasound transducer array over at least a portion of the three-dimensional imaging volume, the active ultrasound transducer array is configured to repeatedly actuate during the first scan to generate a plurality of sequential two-dimensional ultrasound data slices, the processor circuit is configured to execute program instructions to combine the plurality of sequential two-dimensional ultrasound data slices to form three-dimensional ultrasound volumetric data from which a three-dimensional ultrasound image is generated.

9. The ultrasound imaging system of claim 8, the processor circuit configured to execute program instructions to operate the active ultrasound transducer array to generate multiple sets of ultrasound image data that includes metadata corresponding to a particular location, the processor circuit configured to execute program instructions to sum the multiple sets of ultrasound image data to generate composite ultrasound image data.

10. The ultrasound imaging system of claim 8, comprising a third tracking element configured for attachment to the patient, wherein when the third tracking element is energized by the EM field generator, the third tracking element generates three-axis patient location data, which is supplied to the processor circuit, the processor circuit executing program instructions to process the three-axis patient location data and assign location information for images captured by the active ultrasound transducer array to known positions within the virtual 3D environment referenced from the third tracking element.

11. The ultrasound imaging system of claim 8, the processor circuit configured to execute program instructions to render and display at least one synthetic scan plane by defining a desired image plane in the three-dimensional ultrasound volumetric data.

12. The ultrasound imaging system of claim 11, wherein the desired image plane is one of a coronal scan plane and an axial scan plane.

13. The ultrasound imaging system of claim 8, wherein the processor circuit is configured to execute program instructions to determine a region of interest in the three-dimensional ultrasound volumetric data defining the three-dimensional imaging volume, and the processor circuit is configured to execute program instructions to produce a second scan with a second scan range of the active ultrasound transducer array of the ultrasound transducer mechanism for acquisition of subsequent three-dimensional ultrasound volumetric data at the region of interest, wherein the second scan range is reduced from that of the scan range of the first scan.

14. The ultrasound imaging system of claim 8, wherein the processor circuit is configured to execute program instructions to generate a first two-dimensional ultrasound image slice from a series of two-dimensional ultrasound image slices in the three-dimensional ultrasound volumetric data, the first two-dimensional ultrasound image slice including a particular region of interest, the first two-dimensional ultrasound image slice lying in a first imaging plane different from that of the imaging plane of the series of two-dimensional ultrasound image slices, and further comprising a graphical user interface communicatively coupled to the processor circuit, the graphical user interface having at least one slice selection slider configured to provide a sequential parallel variation from the first two-dimensional ultrasound image slice to manually select a second two-dimensional ultrasound image slice parallel to the first two-dimensional ultrasound image, wherein the second two-dimensional ultrasound image slice lies on either side of the first two-dimensional ultrasound image slice.

15. The ultrasound imaging system of claim 14, wherein the particular region of interest includes the distal tip of the interventional medical device.

16. The ultrasound imaging system of claim 1, wherein the processor circuit is configured to generate the positioning signal to dynamically adjust in near real time the active ultrasound transducer array of the ultrasound probe to the desired imaging location to maintain the distal tip of the interventional medical device within the three-dimensional imaging volume.

17. The ultrasound imaging system of claim 16, wherein the processor circuit is configured to adapt the positioning signal based on a change in position of the ultrasound probe.

18. The ultrasound imaging system of claim 16, wherein the processor circuit is configured to adapt the positioning signal based on the tip location data relating to the first tracking element of the interventional medical device.

19. The ultrasound imaging system of claim 16, wherein the processor circuit is configured to adapt the positioning signal based on a change in a patient's position.

20. The ultrasound imaging system of claim 1, wherein the head portion having a planar surface, the planar surface having an origin point, wherein the processor circuit is configured to execute program instructions to define a unit vector that begins at the origin point, the unit vector extends downwardly at a perpendicular angle to the planar surface, the processor circuit is configured to execute program instructions to calculate the ultrasound plane position based on the probe location data with respect to the origin point.

* * * * *